US008580795B2

(12) United States Patent
Balasubramanian et al.

(10) Patent No.: US 8,580,795 B2
(45) Date of Patent: Nov. 12, 2013

(54) HETEROCYCLIC COMPOUNDS AS PHOSPHODIESTERASE INHIBITORS

(75) Inventors: Gopalan Balasubramanian, Chennai (IN); Sukunath Narayanan, Chennai (IN); Ganapavarapu Veera Raghava Sharma, Vishakhapatnam (IN); Lavanya Andiappan, Chennai (IN); Shridhar Narayanan, Chennai (IN); Sanjeev Saxena, Chennai (IN); Sridharan Rajagopal, Chennai (IN); Santosh Lolaknath Vishwakarma, Chennai (IN); Saravanan Thirunavukkarasu, Chennai (IN)

(73) Assignee: Orchid Chemicals & Pharmaceuticals Limited, Chennai (IN)

( * ) Notice: Subject to any disclaimer, the term of this patent is extended or adjusted under 35 U.S.C. 154(b) by 159 days.

(21) Appl. No.: 13/143,480

(22) PCT Filed: Jan. 21, 2010

(86) PCT No.: PCT/IB2010/000094
§ 371 (c)(1),
(2), (4) Date: Jul. 6, 2011

(87) PCT Pub. No.: WO2010/084402
PCT Pub. Date: Jul. 29, 2010

(65) Prior Publication Data
US 2011/0269753 A1 Nov. 3, 2011

(30) Foreign Application Priority Data

Jan. 22, 2009 (IN) .............................. 143/CHE/2009

(51) Int. Cl.
*A61K 31/496* (2006.01)
*C07D 405/14* (2006.01)

(52) U.S. Cl.
USPC ..................... 514/252.19; 544/364

(58) Field of Classification Search
USPC ..................... 514/252.19; 544/364
See application file for complete search history.

(56) References Cited

U.S. PATENT DOCUMENTS 3,872,094 A    3/1975   Meyer
5,587,112 A   12/1996   Kauffman et al.

FOREIGN PATENT DOCUMENTS

CH           532 629         1/1973
EP         0 952 149 A2     10/1999
WO       WO 02/079154 A1    10/2002

OTHER PUBLICATIONS

Jul. 26, 2011 International Preliminary Report on Patentability and Written Opinion issued in International Application No. PCT/IB2010/000094.

Routier et al., "Oxygen heterocycles. Part VI. Orientation in the Substitution of 2-Methoxydibenzofuran," *Journal of the Chemical Society*, Jan. 1, 1956, pp. 4276-4279.
Celli, "COPD, Inflammation and Its Modulation by Phosphodiesterase 4 Inhibitors," *Chest Journal*, Jan. 2006, pp. 5-6, vol. 129, Issue 1, American College of Chest Physicians.
Rogers et al., "Asthma therapy for the 21$^{st}$ century," *Trends in Pharmacological Sciences*, May 1998, pp. 160-164, vol. 19, Elsevier Science Ltd.
Barnes, "Chronic obstructive pulmonary disease: new opportunities for drug development," *Trends in Pharmacological Science*, Oct. 1998, pp. 415-423, vol. 19, Elsevier Science Ltd.
Pages et al., "PDE4 inhibitors: a review of current developments (2005-2009)," *Expert Opinion on Therapeutic Patents*, 2009, pp. 1501-1519, vol. 19, Issue 11, Informa UK Ltd.
Torphy, "Phosphodiesterase Isozymes: Molecular Targets for Novel Antiasthma Agents," *American Journal of Respiratory and Critical Care Medicine*, 1998, pp. 351-370, vol. 157.
Barnes, "New approaches to COPD," *European Respiratory Review*, 2005, pp. 2-11, vol. 14, Issue 94, ERSJ.
Bäumer et al., "Highly Selective Phosphodiesterase 4 Inhibitors for the Treatment of Allergic Skin Diseases and Psoriasis," *Inflammation & Allergy—Drug Targets*, 2006, pp. 17-26, vol. 6, Bentham Science Publishers Ltd.
Cheng et al., "Cyclic Nucleotide Phosphodiesterase (PDE) Inhibitors: Novel Therapeutic Agents for Progressive Renal Disease," *Experimental Biology and Medicine*, 2007, pp. 38-51, vol. 232, Society for Experimental Biology and Medicine.
Raine, "Multiple sclerosis: TNF revisited, with promise," *Nature Medicine*, Mar. 1995, pp. 211-214, vol. 1, Issue 3, Nature Publishing Group.
Sommer et al., "The antidepressant rolipram suppresses cytokine production and prevents autoimmune encephalomyelitis," *Nature Medicine*, Mar. 1995, pp. 244-248, vol. 1, Issue 3, Nature Publishing Group.
Hotamisligil et al., "Reduced Tyrosine Kinase Activity of the Insulin Receptor in Obesity-Diabetes: Central Role of Tumor Necrosis Factor-α," *The Journal of Clinical Investigation*, Oct. 1994, pp. 1543-1549, vol. 94, The American Society for Clinical Investigation, Inc.
Chi et al, "Effects of Rolipram, a Selective Inhibitor of Type 4 Phosphodiesterase, on Lipopolysaccharide-Induced Uveitis in Rats," *Investigative Ophthalmology and Visual Science*, Aug. 2004, pp. 2497-2502, vol. 45, Issue 8, Association for Research in Vision and Ophthalmology.

(Continued)

*Primary Examiner* — Taofiq A Solola
(74) *Attorney, Agent, or Firm* — Oliff & Berridge, PLC

(57) ABSTRACT

Compounds of the formula (I), their derivatives, analogs, tautomeric forms, regioisomers, stereoisomers, polymorphs, solvates, intermediates, pharmaceutically acceptable salts, pharmaceutical compositions, N-oxides, metabolites and prodrugs thereof. These compounds are phosphodiesterase type 4 (PDE4) inhibitors. They are useful in the treatment of a variety of allergic or inflammatory diseases including asthma, COPD, chronic bronchitis, atopic dermatitis, allergic rhinitis, allergic conjunctivitis, vernal conjuctivitis, psoriasis, rheumatoid arthritis, ulcerative colitis, Crohn's disease, uveitis, NASH and lupus.

10 Claims, No Drawings

(56) References Cited

OTHER PUBLICATIONS

Barnette et al., "Inhibitors of Phosphodiesterase IV (PDE IV) Increase Acid Secretion in Rabbit Isolated Gastric Glands: Correlation Between Function and Interaction with a High-Affinity Rolipram Binding Site," *The Journal of Pharmacology and Experimental Therapeutics*, 1995, pp. 1396-1402, vol. 273, Issue 3, The American Society for Pharmacology and Experimental Therapeutics.

Jacobitz at al., "Mapping the Functional Domains of Human Recombinant Phosphodiesterase 4A: Structural Requirements for Catalytic Activity and Rolipram Binding," *Journal of Molecular Pharmacology*, 1996, pp. 891-899, vol. 50, The American Society for Pharmacology and Experimental Therapeutics.

Muller at al., "Subtypes of the type 4 cAMP phosphodiesterases: structure, regulation and selective inhibition," *Trends in Pharmacological Sciences*, Aug. 1996, pp. 294-298, vol. 17, Elsevier Science Ltd.

Hughes et al., "The inhibition of antigen-induced eosinophilia and bronchoconstriction by CDP840, a novel stereo-selective inhibitor of phosphodiesterase type 4," *British Journal of Pharmacology*, 1996, pp. 1183-1191, vol. 118, Stockton Press.

Janský et al., "Dynamics of Cytokine Production in Human Peripheral Blood Mononuclear Cells Stimulated by LPS or Infected by Borrelia," *Physiological Research*, 2003, pp. 593-598, vol. 52, Institute of Physiology.

Bardelle et al. "Phosphodiesterase 4 Conformers: Preparation of Recombinant Enzymes and Assay for Inhibitors," *Analytical Biochemistry*, 1999, pp. 148-155, vol. 275, Issue 2, Academic Press.

Essayan, "Cyclic Nucleotide Phosphodiesterase (PDE) Inhibitors and Immunomodulation," *Biochemical Pharmacology*, 1999, pp. 965-973, vol. 57, Elsevier Science Inc.

Spond et al. "The role of neutrophils in LPS-induced changes in pulmonary function in conscious rats," *Pulmonary Pharmacology & Therapeutics*, 2004, pp. 133-140, vol. 17, Elsevier Ltd.

International Search Report issued in International Application No. PCT/IB2010/000094, mailed Nov. 9, 2010.

HETEROCYCLIC COMPOUNDS AS PHOSPHODIESTERASE INHIBITORS

FIELD

Described are heterocyclic compounds of the formula (I), their derivatives, analogs, tautomeric forms, regioisomers, stereoisomers, polymorphs, solvates, intermediates, pharmaceutically acceptable salts, pharmaceutical compositions, N-oxides, metabolites and prodrugs thereof.

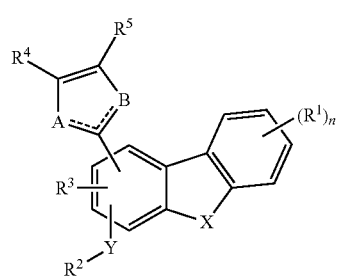

Also described herein is the process for the preparation of the above said novel compounds of formula (I), their analogs, stereoisomers, diastereomers, polymorphs, hydrates, solvates, pharmaceutically acceptable salts, pharmaceutical compositions, metabolites, prodrugs and intermediates useful in the preparation of such compounds.

The compounds described herein are phosphodiesterase type 4 (PDE4) inhibitors. More particularly, they down regulate or inhibit the production of tumor necrosis factor (TNF-α) which are mediated by PDE4 enzymes and therefore are useful in the treatment of a variety of allergic and inflammatory diseases including asthma, COPD, chronic bronchitis, atopic dermatitis, allergic rhinitis, allergic conjunctivitis, vernal conjunctivitis, psoriasis, rheumatoid arthritis, ulcerative colitis, Crohn's disease, uveitis, NASH and lupus.

BACKGROUND

Airway inflammation characterize's a number of severe lung diseases including asthma and chronic obstructive pulmonary disease (COPD). Events leading to airway obstruction include edema of airway walls, infiltration of inflammatory cells into the lungs, production of various inflammatory mediators and increased mucous production. The airways of asthmatic patients are infiltrated by inflammatory leukocytes, of which the eosinophil is the most prominent component. The magnitude of asthmatic reactions is correlated with the number of eosinophils present in the lungs. The accumulation of eosinophils is found dramatically in the lungs of asthmatic patients, which are capable of lysing and activating cells and destroying tissues. Upon activation eosinophils release inflammatory cytokines such as IL-1, IL-1β, IL-3, IL-6, IL-8, IL-12, TNF-α and inflammatory mediators such as PAF (Platelet-Activating Factor), LTD4 (Leukotriene-D4) and relative oxygen species that can produce edema, bronchoconstriction. TNF-α is involved in the pathogenesis of a number of autoimmune and inflammatory diseases (Bartolome Celli, *Chest*, 2006, vol 129 no. 1, 5-6). Consequently, manipulation of the cytokine signaling or biosynthetic pathways associated with these proteins may provide therapeutic benefit in disease states mentioned above. It has been well demonstrated that TNF-α production in pro-inflammatory cells becomes attenuated by an elevation of intracellular cyclic adenosine 3',5'-monophosphate (cAMP); this second messenger is regulated by the phosphodiesterase (PDE) family of enzymes. The phosphodiesterase enzymes play an integral role in cell signaling mechanisms by hydrolyzing cAMP and cGMP to their inactive 5' forms. Inhibition of PDE enzymes thus results in an elevation of cAMP and/or cGMP levels and alters intracellular responses to extra cellular signals by affecting the processes mediated by cyclic nucleotides. Since eosinophils are believed to be a critical proinflammatory target for asthma, identification of the expression of PDE4 gene family in eosinophils led to the PDE4 as potential therapeutic target for asthma [Rogers, D. F., et al., *Trends Pharmacol. Sci.,* 1998, 19, 160-164; Barnes, P. J., Trends Pharmacol. Sci., 1998, 19, 415-423, L. Pages, et. al., *Expert Opin. Ther. Patents* 2009, 19, 1501-1519].

Phosphodiesterase type 4 (PDE4) is cAMP-specific and $Ca^{2+}$ independent enzyme and hydrolyses cAMP in mast cells, basophils, eosinophils, monocytes and lymphocytes. The association between cAMP elevation in inflammatory cells with airway smooth muscle relaxation and inhibition of mediator release has led to widespread interest in the design of PDE4 inhibitors [Trophy, T. J., *Am. J. Respir. Crit. Care Med.,* 1998, 157, 351-370; P. J. Barnes, *Eur Respir Rev* 2005, 14: 94, 2-11; Wolfgang Bäumer et al., *Inflammation & Allergy—Drug Targets,* 2006, 6, 17-26; Joseph P. Grande et al., *Exp Biol Med* 2007, 232, 38-51]. Excessive or unregulated TNF-α production has been implicated in mediating or exacerbating a number of undesirable physiological conditions such as diseases including osteoarthritis and other arthritic conditions; septic shock, endotoxic shock and respiratory distress syndrome. Since TNF-α also participates in the onset and progress of autoimmune diseases, PDE4 inhibitors may find utility as therapeutic agents for rheumatoid arthritis, multiple sclerosis and Crohn's disease. [*Nature Medicine,* 1995, 1, 211-214 and ibid., 244-248]. TNF-α is also reported to be a factor of insulin-resistant diabetes because it declines the phosphorylating mechanism of insulin receptors of muscle and fat cells [*J. Clin. Invest.,* 1994, 94, 1543-1549].

It has been demonstrated that increasing cAMP levels within these cells results in suppression of cell activation, which in turn inhibits the production and release of pro-inflammatory cytokines such as TNF-α. Since eosinophils are believed to be a critical pro-inflammatory target for asthma, identification of the expression of PDE4 gene family in eosinophils led to the PDE4 as potential therapeutic target for asthma. The IL-6, tumor necrosis factor TNF-α, E-selectin, and nitric oxide (NO) production have been reported to be involved in the pathogenesis of LPS-induced uveitis, PDE4 inhibitors are known to suppress cutaneous inflammation and LPS-induced TNF-α expression including IL-6 inhibition, forming a viable strategy for treatment of uveitis (*Investigative Ophthalmology and Visual Science,* 2004, 45, 2497-2502).

Interest in the drugs capable of selective inhibition of PDE4 has taken much attention due to several factors: (a) tissue distribution of PDE-4 strongly suggested that the pathologies related to the central nervous and immune systems could be treated through the selective PDE4 inhibitors (b) increase in intracellular cAMP concentration, the obvious biochemical consequence of PDE-4 inhibition, has been well characterized in immuno-competent cells where it acts as a deactivating signal.

Four human cDNA isoforms of PDE-4 (PDE4-A, B, C and D) were identified. mRNA for all these four isoforms was expressed in the human lungs. PDE4-A, B, C and D were expressed in eosinophils. Of these gene families, PDE-4 characterized as the cAMP-specific gene family has been shown to predominate in proinflammatory human lymphoid and myeloid lineage cells.

Objective

The application of several PDE4 inhibitors is limited due to their undesirable side effect profile, which include nausea, emesis and gastric acid secretion due to action on PDE4 in parietal cells in the gut. [Barnette et al., T. J., *J. Pharmacol. Exp. Ther.*, 1995, 273, 1396-1402]. One of the earliest PDE4 inhibitors, Rolipram, was withdrawn from clinical development because of its severe unacceptable side effect profile. [Zeller E. et al., *Pharmacopsychiatry*, 1984, 17, 188-190]. The cause of the severe side effects of several PDE4 inhibitor molecules in human clinical trials has recently become apparent. [Jacobitz, et al., *J., Mol. Pharmacol.*, 1996, 50, 891-899]. The human recombinant PDE4 exists in four isoforms A, B, C, and D [Muller, T et al., *Trends in Pharmacol. Sciences*, 1996, 17, 294-298] accordingly compounds displaying more PDE4D isoenzyme selectivity over the A, B or C are found to have fewer side effects than Rolipram [Hughes, B et al., *Br. J. Pharmacol.* 1996, 118, 1183-1191]. Therefore, selective inhibitors of PDE4 isozymes would have therapeutic effects in inflammatory and respiratory diseases and fewer undesirable side effects.

Although researchers all over the world are working in this direction to achieve the desired selective PDE4 isozyme inhibition, so far success is limited. Among the various compounds, which showed clinically proven PDE 4 inhibition, Oglemilast, Apremilast and ELB-353 have reached advanced stage of human clinical trials.

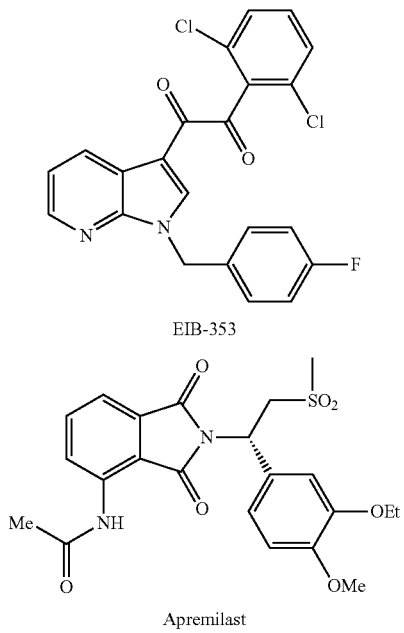

EIB-353

Apremilast

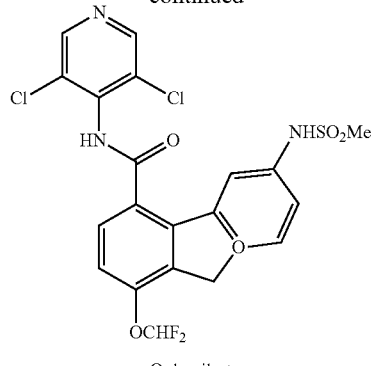

Oglemilast

Described herein is the use of therapeutically effective amount of the compounds of the general formula (I) or a pharmaceutically acceptable salt thereof as a medicament for therapeutic treatment of PDE4 and TNF-α mediated diseases such as asthma, COPD and chronic inflammatory diseases, specific autoimmune diseases, sepsis-induced organ injury, in the subjects like human beings and animals.

SUMMARY

Described are compounds of the general formula (I),

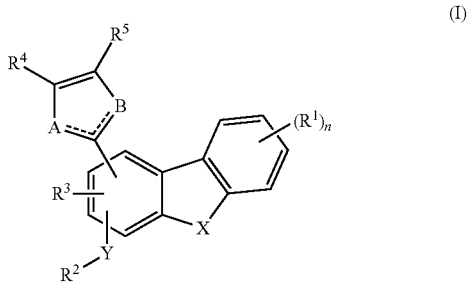

their derivatives, analogs, tautomeric forms, regioisomers, stereoisomers, polymorphs, solvates, intermediates, pharmaceutically acceptable salts, pharmaceutical compositions, N-oxides, metabolites and prodrugs thereof,
wherein: X and Y independently represents O, S or $NR^6$;
$R^1$, $R^3$, $R^4$ and $R^5$ may be same or different and independently represents hydrogen, halogen, haloalkyl, nitro, cyano, hydroxy, substituted or unsubstituted groups selected from alkyl, alkylthio, alkoxy, aryl, aryloxy, aralkyl, alkenyl, alkynyl, aralkenyl, aralkynyl, cycloalkyl, cycloalkenyl, cycloalkynyl, heterocyclyl, heteroaryl, heteroarylalkyl, $-(CH_2)_m-CONR^7R^8$, amino, imino, alkylamino, cycloalkylamino, arylamino, aralkylamino, alkanoyl, aroyl, aralkanoyl, sulfonyl, alkylsulfonyl, aryl sulfonyl, aminosulfonyl, $-COOR^7$, $-C(O)R^7$, $-C(S)R^7$, $-C(O)NR^7R^8$, $-NR^7C(O)NR^7R^8$, $-N(R^7)SOR^8$, $-N(R^7)SO_2R^8$, $-NR^7C(O)OR^8$, $-NR^7R^8$, $-NR^7C(O)R^8$, $-NR^7C(S)R^8$, $-SONR^7R^8$, $-SO_2NR^7R^8$; $-OR^7$, $-OR^7C(O)OR^8$, $-CONR^7OR^8$, $-C(O)R^7$, $-OC(O)NR^{70}$, $-R^7NR^7R^8$, $-R^7OR^8$, $-SR^7$, $-SOR^7$ and $-SO_2R^7$; $R^7$ and $R^8$ each independently represents hydrogen, substituted or unsubstituted groups selected from alkyl, aryl, aralkyl, cycloalkyl, heterocyclyl, heteroaryl and heteroarylalkyl or $R^7$ and $R^8$ can be combined together to form an substituted or unsubstituted 3-7 membered ring having 0-2 hetero atoms;

$R^4$ and $R^5$ can be combined together to form a substituted or unsubstituted 5 to 7 membered ring, having 0-3 heteroatoms selected from O, N and S;

$R^2$ represents substituted or unsubstituted groups selected from alkyl, haloalkyl, cycloalkyl and the like;

A or B represents —$CR^6$, $NR^6$, =N—, —O— or —S—; when one of A or B represents —$CR^6$, then the other represents —$NR^6$—, —O— or —S—;

$R^6$ represents hydrogen, substituted or unsubstituted groups selected from alkyl, cycloalkyl, cycloalkenyl, cycloalkynyl, aryl, aralkyl, alkenyl, alkynyl, aralkenyl, aralkynyl, heterocyclyl and heteroaryl;

when X is $NR^6$, then $R^2$ and $R^6$ can be combined together to form a substituted or unsubstituted 5 to 7 membered ring having 0-3 heteroatoms selected from O, N and S;

' ---- ' represents a double bond or a single bond;

m and n are integers independently selected from 0, 1, 2, 3 or 4.

DETAILED DESCRIPTION

Described are compounds of the general formula (I), (I)

their derivatives, analogs, tautomeric forms, regioisomers, stereoisomers, polymorphs, solvates, intermediates, pharmaceutically acceptable salts, pharmaceutical compositions, N-oxides, metabolites and prodrugs thereof, wherein X and Y independently represents O, S or $NR^6$;

$R^1$, $R^3$, $R^4$ and $R^5$ may be same or different and independently represents hydrogen, halogens such as fluorine, chlorine, bromine and iodine; haloalkyl group such as difluoromethyl, dichloromethyl, trifluoromethyl, tribromomethyl, trichloromethyl and the like; nitro, cyano, hydroxy, optionally substituted groups selected from alkyl, alkylthio, alkoxy, aryl, aryloxy, aralkyl, alkenyl, alkynyl, aralkenyl, aralkynyl, cycloalkyl, cycloalkenyl, cycloalkynyl, heterocyclyl, heteroaryl, heteroarylalkyl, —$(CH_2)_m$—$C(O)NR^7R^8$, amino, imino, alkylamino, cycloalkylamino, arylamino, aralkylamino, alkanoyl, aroyl, aralkanoyl, sulfonyl, alkylsulfonyl groups such as methylsulfonyl, ethylsulfonyl, n-propylsulfonyl, iso-propylsulfonyl and the like; arylsulfonyl groups such as phenylsulfonyl, naphthylsulfonyl and the like; aminosulfonyl, alkylsulfonamido, —$COOR^7$, —$C(O)R^7$, —$C(S)R^7$, —$C(O)NR^7R^8$, —$NR^7C(O)NR^7R^8$, —$N(R^7)SOR^8$, —$N(R^7)SO_2R^8$, —$NR^7C(O)OR^8$, —$NR^7R^8$, —$NR^7C(O)R^8$, —$NR^7C(S)R^8$, —$SONR^7R^8$, —$SO_2NR^7R^8$; —$OR^7$, —$OR^7C(O)OR^8$, —$CONR^7OR^8$, —$OC(O)R^7$, —$OC(O)NR^7R^8$, —$R^7NR^7R^8$, —$R^7OR^8$, —$SR^7$, —$SOR^7$ and —$SO_2R^7$; $R^7$ and $R^8$ each independently represents hydrogen, substituted or unsubstituted groups selected from alkyl, aryl, aralkyl, cycloalkyl, heterocyclyl, heteroaryl and heteroarylalkyl or $R^7$ and $R^8$ can be combined together to form an substituted or unsubstituted 3-7 membered ring having 0-2 hetero atoms;

$R^4$ and $R^5$ can be combined together to form a substituted or unsubstituted 5 to 7 membered ring, having 0-3 heteroatoms selected from O, N and S;

$R^2$ represents substituted or unsubstituted groups selected from alkyl, haloalkyl, cycloalkyl;

when X is $NR^6$, then $R^2$ and $R^6$ can be combined together to form a substituted or unsubstituted 5 to 7 membered ring having 0-3 heteroatoms selected from O, N and S;

' ---- ' represents a double bond or a single bond.

A or B represents —$CR^6$, $NR^6$, =N—, —O— or —S—; when one of A or B represents —$CR^6$, then the other represents —$NR^6$, =N—, —O— or —S—;

$R^6$ represents hydrogen, optionally substituted groups selected from alkyl, cycloalkyl, cycloalkenyl, cycloalkynyl, aryl, aralkyl, alkenyl, alkynyl, aralkenyl, aralkynyl, heterocyclyl or heteroaryl;

m and n are integers independently selected from 0, 1, 2, 3 or 4.

The term "substituted" as used herein refers to substitution with any one or any combination of the following substituents: halogens comprising fluorine, chlorine, bromine and iodine; hydroxy; nitro; cyano; oxo (=O); thioxo (=S); azido; nitroso; amino; hydrazino; formyl; alkyl; haloalkyl groups such as trifluoromethyl, tribromomethyl and trichloromethyl; haloalkoxy groups such as chloromethoxy, chloroethoxy, difluoromethoxy, dichloromethoxy, trifluoromethoxy, trifluoroethoxy, trichloromethoxy and the like; arylalkoxy groups such as benzyloxy and phenylethoxy; cycloalkyl; —O-cycloalkyl; aryl; alkoxy; heterocyclyl; heteroaryl; alkylamino; —O—$CH_2$-cycloalkyl; —$COOR^a$; —$C(O)R^b$; —$C(S)R^a$; —$C(O)NR^aR^b$; —$NR^aC(O)NR^bR^c$; —$N(R^a)SOR^b$; —$N(R^a)SO_2R^b$; —$NR^aC(O)OR^b$; —$NR^aR^b$; —$NR^aC(O)R^b$; —$NR^aC(S)R^b$; —$SONR^aR^b$; —$SO_2NR^aR^b$; —$OR^a$; —$OR^aC(O)OR^b$; —$OC(O)NR^aR^b$; —$OC(O)R^a$; —$R^aNR^bR^c$; —$R^aOR^b$; —$SR^a$; —$SOR^a$ and —$SO_2R^a$; $R^a$, $R^b$ and $R^c$ each independently represents hydrogen atom; substituted or unsubstituted groups selected from alkyl, alkylene; aryl; aralkyl; cycloalkyl; heterocyclyl; heteroaryl or heteroarylalkyl; $R^a$, $R^b$ and $R^c$ can be combined together to form a 3-7 membered ring having 0-2 hetero atoms; the substituents are further optionally substituted by one or more substituents as defined above.

The term "alkyl" refers to straight or branched aliphatic hydrocarbon groups having the specified number of carbon atoms, which are attached to the rest of the molecule by a single atom. Preferred alkyl groups include, without limitation, methyl, ethyl, n-propyl, isopropyl, butyl, isobutyl, t-butyl, pentyl, hexyl, heptyl, octyl and the like.

The term "alkenyl" refers to an aliphatic hydrocarbon group containing a carbon-carbon double bond, which may be straight or branched chain having about 2 to 10 carbon atoms, which may be optionally substituted by one or more substituents. Preferred alkenyl groups include, without limitation, ethenyl, 1-propenyl, 2-propenyl, 2-methyl-1-propenyl, 1-butenyl, 2-butenyl and the like.

The term "alkynyl" refers to straight or branched hydrocarbyl radicals having at least one carbon-carbon triple bond in the range of 2-12 carbons. Preferred alkynyl groups include, without limitation, ethynyl, propynyl, butynyl and the like.

The term "aryl" refers to aromatic radicals having 6 to 14 carbon atoms, which may be optionally substituted by one or more substituents. Preferred aryl groups include, without limitation, phenyl, naphthyl, indanyl, biphenyl and the like or substituted or unsubstituted arylene groups such as phenylene, biphenylene, naphthylene, anthracenylene, phenanthrylene, indanylene and the like.

The term "aralkyl" refers to an aryl group directly bonded to an alkyl group, which may be optionally substituted by one or more substituents. Preferred aralkyl groups include, without limitation, —CH$_2$C$_6$H$_5$, —C$_2$H$_4$C$_6$H$_5$ and the like.

The term "aralkenyl" refers to an aromatic ring radical directly bonded to an alkenyl group. The aryl radical may be attached to the main structure at any carbon from the alkenyl group. Examples of such aralkenyl groups include but are not limited to, phenylethenyl and phenylpropenyl.

The term "aralkynyl" refers to an aromatic ring radical directly bonded to an alkynyl group. The aryl radical may be attached to the main structure at any carbon from the alkynyl group. Examples of such aralkynyl groups include but are not limited to, phenylethynyl and phenylpropynyl.

The term "alkanoyl" represents a group of the formula —C(O)alkyl. Preferred alkanoyl groups include, without limitation, acetyl, propanoyl, butanoyl and the like.

The term "aroyl" denotes an aryl-CO— group, wherein aryl is as defined above. Examples of such aroyl groups include but are not limited to, benzoyl, naphthoyl and the like.

The term "aralkanoyl" refers to aralkyl-C(O)— group. Examples of such aralkanoyl groups include but are not limited to, phenylacetyl, phenylpropanoyl, naphthylacetyl, naphthylpropanoyl and the like.

The term "heterocyclyl" refers to a stable 3-15 membered ring radical, which consists of carbons and from 1-5 heteroatoms selected from nitrogen, phosphorus, oxygen and sulfur. For purposes of this invention the heterocyclic ring radical may be monocyclic, bicyclic or tricyclic ring system and nitrogen, phosphorus, carbon, oxygen or sulfur atoms in the heterocyclic ring radical may be optionally oxidized to various oxidation states. In addition, the nitrogen atom may be optionally quaternized and the ring radical may be partially or fully saturated. Preferred heterocyclyl groups include, without limitation, azetidinyl, acridinyl, benzodioxolyl, benzodioxanyl, benzofuranyl, carbazolyl, cinnolinyl, dioxolanyl, dibenzofuranyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazolyl, imidazolyl, tetrahydroisoquinolinyl, piperidinyl, piperazinyl, homopiperazinyl, 2-oxoazepinyl, azepinyl, pyrrolyl, 4-piperidonyl, pyrazinyl, pyrimidinyl, pyridazinyl, oxazolyl, oxazolinyl, triazolyl, isoxazolyl, isoxazolidinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, decahydroisoquinolyl, benzimidazolyl, thiadiazolyl, benzopyranyl, benzothiazolyl, benzooxazolyl, thienyl, morpholinyl, thiomorpholinyl, thiamorpholinyl sulfoxide, furyl, tetrahydrofuryl, tetrahydropyranyl, chromanyl and isochromanyl. The heterocyclyl ring radical may be attached to the main structure at any heteroatom or carbon that results in the creation of a stable structure.

The term "heteroaryl" refers to an aromatic heterocyclic ring radical as defined above. The heteroaryl ring radical may be attached to the main structure at any heteroatom or carbon atom that results in the creation of a stable structure.

The term "heteroarylalkyl" refers to a heteroaryl ring radical as defined above, directly bonded to an alkyl group. The heteroarylalkyl radical may be attached to the main structure at any carbon atom from an alkyl group.

The term "cycloalkyl" refers to non-aromatic mono or polycyclic ring systems of about 3 to 12 carbon atoms. Preferred cycloalkyl groups include, without limitation, cyclopropyl, cyclobutyl, cyclopentyl, cyclohexyl, cyclooctanyl and the like; preferred polycyclic rings include, without limitation, perhydronaphthyl, adamantyl and norbornyl groups, bridged cyclic groups or spirobicyclic groups e.g. spiro[4.4]-non-2-yl and the like.

The term "cycloalkenyl" refers to a non-aromatic cyclic ring radical containing about 3 to 8 carbons with at least one carbon-carbon double bond, which may be optionally substituted. Preferred cycloalkenyl groups include, without limitation, cyclopropenyl, cyclopentenyl and the like.

The term "cycloalkynyl" refers to a non-aromatic cyclic ring radical containing about 3 to 8 carbon atoms with at least one carbon-carbon triple bond, which may be optionally substituted. Preferred cycloalkynyl groups include, without limitation, cyclopropynyl, cyclopentynyl and the like.

The term "alkylthio" refers to an alkyl group attached via a sulfur linkage to the rest of the molecule, which may be optionally substituted. Preferred alkylthio groups include, without limitation, —SCH$_3$, —SC$_2$H$_5$ and the like.

The term "alkoxy" refers to an alkyl group attached via an oxygen linkage to the rest of the molecule. Preferred alkoxy groups include, without limitation, —OCH$_3$, —OC$_2$H$_5$ and the like.

The term "aryloxy" refers to an aryl group attached via an oxygen linkage to the rest of the molecule. Preferred aryloxy groups include, without limitation, —O-phenyl, —O-biphenyl and the like.

The term "alkylamino" refers to an alkyl group as defined above attached via an amino linkage to the rest of the molecule. Preferred alkylamino groups include, without limitation, —NHCH$_3$, —N(CH$_3$)$_2$ and the like.

The term "alkylsulfonyl" refers to straight or branched hydrocarbyl radicals group attached via a —SO$_2$— linkage to the rest of the molecule. Preferred alkylsulfonyl groups include without limitation methylsulfonyl, ethylsulfonyl, n-propylsulfonyl or isopropylsulfonyl.

The term "arylsulfonyl" refers to an aryl group attached via a —SO$_2$— linkage to the rest of the molecule. Preferred arylsulfonyl groups include without limitation phenylsulfonyl or naphthylsulfonyl.

The term "arylamino" refers to an aryl group attached via a amino linkage to the rest of the molecule. Preferred arylamino groups include without limitation phenylamino or naphthylamino.

The term "ring" refers to substituted or unsubstituted monocyclic or polycyclic, saturated or partially saturated or aromatic containing 0 to 4 heteroatoms selected from O, S and N.

The term "metabolite", as used herein, refers to a derivative of a compound of formula (I) which is formed when the compound is metabolized.

The term "prodrug", as employed herein, denotes a compound that is a drug precursor which, upon administration to a subject, undergoes chemical conversion by metabolic or chemical processes to yield a compound of formula (I).

The term "tautomer", as used herein, refers to one of two or more structural isomers which exist in equilibrium and which are readily converted from one isomeric form to another.

The term "derivative" refers to a chemical compound or molecule made from a parent compound by one or more chemical reactions such as, by oxidation, hydrogenation, alkylation, esterification, halogenation and the like.

Furthermore, the compound of formula (I) can be its derivatives, analogs, tautomeric forms, stereoisomers, geometrical isomers, polymorphs, solvates, N-oxides, intermediates, pharmaceutically acceptable salts, pharmaceutical compositions, metabolites and prodrugs.

Pharmaceutically acceptable solvates may be hydrates or comprising of other solvents of crystallization such as alcohols.

Compounds disclosed herein may exist as single stereoisomers, racemates and or mixtures of enantiomers and/or diastereomers. All such single stereoisomers, racemates and mixtures thereof are intended to be within the scope of the subject matter described.

The phrase "pharmaceutically acceptable" refers to compounds or compositions that are physiologically tolerable and do not typically produce allergic or similar untoward reactions, including but are not limited to, gastric upset or dizziness when administered to mammals.

Pharmaceutically acceptable salts include salts derived from inorganic bases such as Li, Na, K, Ca, Mg, Fe, Cu, Zn and Mn; salts of organic bases such as N,N'-diacetylethylenediamine, glucamine, triethylamine, choline, dicyclohexylamine, benzylamine, trialkylamine, thiamine, guanidine, diethanolamine, α-phenylethylamine, piperidine, morpholine, pyridine, hydroxyethylpyrrolidine, hydroxyethylpiperidine and the like, ammonium, substituted ammonium salts, aluminum salts. Salts also include amino acid salts such as glycine, alanine, cystine, cysteine, lysine, arginine, phenylalanine, guanidine etc. Salts may include acid addition salts where appropriate which are sulphates, nitrates, phosphates, perchlorates, borates, hydrohalides, acetates, tartrates, maleates, citrates, succinates, palmoates, methanesulphonates, tosylates, benzoates, salicylates, hydroxynaphthoates, benzenesulfonates, ascorbates, glycerophosphates and ketoglutarates.

The active compounds disclosed can also be prepared in any solid or liquid physical form, for example the compound can be in a crystalline form, in amorphous form and have any particle size. Furthermore, the compound particles may be micronized or nanoized, or may be agglomerated, particulate granules; powders, oils, oily suspensions or any other form of solid or liquid physical forms.

Described herein are also pharmaceutical compositions, containing one or more of the compounds of the formula (I), as defined above, their derivatives, analogs, tautomeric forms, stereoisomers, polymorphs, hydrates, metabolites, prodrugs, pharmaceutically acceptable salts, pharmaceutically acceptable solvates in combination with the usual pharmaceutically employed carriers, diluents and the like, useful for the treatment of inflammatory diseases.

The pharmaceutical composition may be in the forms normally employed, such as tablets, capsules, powders, syrups, solutions, suspensions and the like, may contain flavorants, sweeteners etc. in suitable solid or liquid carriers or diluents, or in suitable sterile media to form injectable solutions or suspensions. The compositions may be prepared by processes known in the art. Suitable pharmaceutically acceptable carriers include solid fillers or diluents and sterile aqueous or organic solutions. The active compound will be present in such pharmaceutical compositions in the amounts sufficient to provide the desired dosage in the range as described above. Suitable routes of administration include systemic, such as orally or by parenteral administration such as subcutaneous, intramuscular, intravenous and intradermal routes. Thus for oral administration, the compounds can be combined with a suitable solid or liquid carrier or diluent to form capsules, tablets, powders, syrups, solutions, suspensions and the like. The pharmaceutical compositions, may, if desired, contain additional components such as flavorants, sweeteners, excipients and the like. For parenteral administration, the compounds can be combined with a sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or alkali or alkaline earth metal salts of the compounds. The injectable solutions prepared in this manner can then be, administered intravenously, intraperitoneally, subcutaneously or intramuscularly.

The compounds of the formula (I) are effective in inhibiting or lowering levels of TNF-α, a important mediator in cellular and molecular process leading to inflammatory and allergic disorders.

Described herein are compounds of formula (I), which is effective in the treatment of allergic and inflammatory diseases or disorder or conditions which may be associated with an undesirable inflammatory immune response or associated with the increase in secretion of TNF-α and/or PDE4 which comprises administering to a subject a therapeutically effective amount of a compound of formula (I).

Also described herein is the method of treating an inflammatory condition or immune disorder in a subject in need thereof, which comprises administering to the subject a therapeutically effective amount of a compound of formula (I). Examples of inflammatory or immune disorders are selected from asthma, COPD (chronic obstructive pulmonary disease), atopic dermatitis, allergic rhinitis, allergic conjunctivitis, psoriasis, rheumatoid arthritis, septic shock, ulcerative colitis, Crohn's disease, multiple sclerosis, rheumatoid spondylitis, osteoarthritis, uveitis eosinophilic granuloma, cystic fibrosis, chronic bronchitis, Lupus and Nonalcoholic steatohepatitis (NASH).

Described herein are compounds of formula (I), which are effective in the treatment and/or prophylaxis, the inflammatory and/or allergic diseases preferably COPD (Chronic obstructive pulmonary disease), asthma, rheumatoid arthritis, allergic rhinitis or uveitis, which comprises administering to a subject a therapeutically effective amount of a compound according to formula (I).

Described herein are compounds of formula (I), which are effective in treating diseases mediated by PDE4, which comprises administering to a subject a therapeutically effective amount of a compound according to formula (I).

A method of treating inflammatory diseases mediated by PDE4 enzyme comprising administering an effective amount of a compound of formula (I), to the mammal in need thereof.

A method of treatment of allergic or inflammatory diseases mediated by PDE4 comprising asthma, COPD, chronic bronchitis, atopic dermatitis, allergic rhinitis, allergic conjunctivitis, vernal conjunctivitis, psoriasis, rheumatoid arthritis, ulcerative colitis, Crohn's disease, uveitis, NASH and lupus administering an effective amount of a compound of formula (I).

A method of treating inflammatory or immunological diseases by lowering plasma concentrations of anyone or a combination or all of TNF-α, IL-1β and IL-6 comprising administering an effective amount of a compound of formula (I), to the mammal in need thereof.

A method of treating immunological diseases, those mediated by cytokines selected from TNF-α, IL-1β, IL-6 and IL-12 comprising administering an effective amount of a compound of formula (I), to the mammal in need thereof.

A method of reducing inflammation in an inflamed organ or tissue by delivering a required amount of compound of formula (I).

The compounds of the formula (I) can also be administered as a pharmaceutical composition in a pharmaceutically acceptable carrier, preferably formulated for oral administration.

The compounds described herein may also exhibit polymorphism. This invention further includes different polymorphs of the compounds. The term polymorph refers to a particular crystalline state of a substance, having particular physical properties such as X-ray diffraction, IR spectra, melting point and the like.

This invention, in addition to the above listed compounds, is intended to encompass the use of analogs of such compounds. In this context, analogs are molecules having substantial biological similarities regardless of structural similarities.

The term "therapeutically effective amount" or "effective amount" is an amount sufficient to effect beneficial or desired results. An effective amount can be administered in one or more administrations. An effective amount is typically sufficient to palliate, ameliorate, stabilize, reverse, slow or delay the progression of the disease state.

The term "subject" as used herein is meant to include all mammals and in particular humans, in need of treatment. The therapeutically effective amount will vary depending upon the subject and disease condition being treated, the weight and age of the subject, the severity of the disease condition, the particular compound of formula (I) chosen, the dosing regimen to be followed, timing of administration, the manner of administration and the like, all of which can readily be determined by one of ordinary skill in the art.

A term once described, the same meaning applies for it, throughout the patent. Representative compounds include:

1. Ethyl 6-(2-(4-methoxydibenzo[b,d]furan-1-yl)-1,3-thiazol-4-yl)picolinate;
2. 6-(2-(4-Methoxydibenzo[b,d]furan-1-yl)-1,3-thiazol-4-yl)picolinic acid;
3. Ethyl 6-(2-(4-ethoxydibenzo[b,d]furan-1-yl)-1,3-thiazol-4-yl)picolinate;
4. 6-(2-(4-Ethoxydibenzo[b,d]furan-1-yl)-1,3-thiazol-4-yl)picolinic acid;
5. Ethyl 6-(2-(4-(difluoromethoxy)dibenzo[b,d]furan-1-yl)-1,3-thiazol-4-yl)picolinate;
6. 6-(2-(4-(Difluoromethoxy)dibenzo[b,d]furan-1-yl)-1,3-thiazol-4-yl)picolinic acid;
7. 6-(2-(6-Fluoro-1-methoxy-9-methyl-9H-carbazol-4-yl)-1,3-thiazol-4-yl)picolinic acid;
8. 4-(2-(4-Methoxydibenzo[b,d]furan-1-yl)-1,3-thiazol-4-yl)benzonitrile;
9. 6-(2-(4-Methoxydibenzo[b,d]furan-2-yl)-1,3-thiazol-4-yl)picolinic acid;
10. 6-(2-(4-Methoxy-8-(methylsulfonamido)dibenzo[b,d]furan-2-yl)-1,3-thiazol-4-yl)picolinic acid;
11. N-(3,5-Dichloropyridin-4-yl)-3-(2-(4-methoxydibenzo[b,d]furan-1-yl)-1,3-thiazol-4-yl)propanamide;
12. N-(3,5-Dichloropyridin-4-yl)-2-(2-(4-methoxydibenzo[b,d]furan-1-yl)-1,3-thiazol-4-yl)acetamide;
13. N-(3,5-Dichloropyridin-4-yl)-2-(4-methoxydibenzo[b,d]furan-1-yl)-1,3-thiazole-4-carboxamide;
14. N-(3,5-dichloropyridin-4-yl)-2-(4-(difluoromethoxy)dibenzo[b,d]furan-1-yl)-1,3-thiazole-4-carboxamide;
15. Ethyl 2-(4-methoxydibenzo[b,d]furan-1-yl)-1,3-thiazole-4-carboxylate;
16. 2-(4-Methoxydibenzo[b,d]furan-1-yl)-1,3-thiazole-4-carboxylic acid;
17. 2-(4-Methoxydibenzo[b,d]furan-1-yl)-N-phenyl-1,3-thiazole-4-carboxamide;
18. (2-(4-Methoxydibenzo[b,d]furan-1-yl)-1,3-thiazol-4-yl)(4-(pyrimidin-2-yl)piperazin-1-yl)methanone;
19. (2-(4-Methoxydibenzo[b,d]furan-1-yl)-1,3-thiazol-4-yl)(4-(pyridin-2-yl)piperazin-1-yl)methanone;
20. N-(4-Chlorophenyl)-2-(4-methoxydibenzo[b,d]furan-1-yl)-1,3-thiazole-4-carboxamide;
21. Ethyl 2-(4-methoxydibenzo[b,d]furan-1-yl)-4-methyl-1,3-thiazole-5-carboxylate;
22. 2-(4-Methoxydibenzo[b,d]furan-1-yl)-4-(4-methoxyphenyl)-1,3-thiazole;
23. 2-(4-Methoxydibenzo[b,d]furan-1-yl)-4-methyl-1,3-thiazole-5-carboxylic acid;
24. N-(3,5-Dichloropyridin-4-yl)-2-(4-methoxydibenzo[b,d]furan-1-yl)-4-methyl-1,3-thiazole-5-carboxamide;
25. 2-(4-Methoxydibenzo[b,d]furan-1-yl)-1,3-thiazole-4-carboxamide;
26. N-Cyclopentyl-2-(4-methoxydibenzo[b,d]furan-1-yl)-5-methyl-1,3-thiazole-4-carboxamide;
27. N-(4-Hydroxycyclohexyl)-2-(4-methoxydibenzo[b,d]furan-1-yl)-5-methyl-1,3-thiazole-4-carboxamide;
28. N-(3,5-Dichloropyridin-4-yl)-2-(4-methoxydibenzo[b,d]furan-1-yl)-5-methyl-1,3-thiazole-4-carboxamide;
29. N-Ethyl-2-(4-methoxydibenzo[b,d]furan-1-yl)-5-methyl-1,3-thiazole-4-carboxamide;
30. 2-(4-Methoxydibenzo[b,d]furan-1-yl)-N-morpholino-1,3-thiazole-4-carboxamide;
31. N-(4-Hydroxycyclohexyl)-2-(4-methoxydibenzo[b,d]furan-1-yl)-1,3-thiazole-4-carboxamide;
32. 2-[4-(Difluoromethoxy)-8-nitrodibenzo[b,d]furan-1-yl]-5-methyl-1,3-thiazole-4-carboxylic acid;
33. 2-(4-(Difluoromethoxy)-8-(methylsulfonamido)dibenzo[b,d]furan-1-yl)-5-methyl-1,3-thiazole-4-carboxylic acid;
34. N-(3,5-Dichloropyridin-4-yl)-2-(4-(difluoromethoxy)-8-methylsulfonamido)dibenzo[b,d]furan-1-yl)-1,3-thiazole-4-carboxamide;
35. 2-(4-(Difluoromethoxy)-8-(methylsulfonamido)dibenzo[b,d]furan-1-yl)-N-(4-hydroxycyclohexyl)-5-methyl-1,3thiazole-4-carboxamide;
36. 2-[8-(Acetylamino)-4-(difluoromethoxy)dibenzo[b,d]furan-1-yl]-1,3-thiazole-4-carboxylic acid;
37. 2-(4-(Difluoromethoxy)-8-(methylsulfonamido)dibenzo[b,d]furan-1-yl)-N-methoxy-5-methyl-1,3-thiazole-4-carboxamide;
38. 2-(8-Acetamido-4-(difluoromethoxy)dibenzo[b,d]furan-1-yl)-N-(4-hydroxycyclohexyl)-1,3-thiazole-4-carboxamide;
39. 2-((4-Difluoromethoxy)dibenzo[b,d]furan-1-yl)-N-(4-hydroxycyclohexyl)-1,3-thiazole-4-carboxamide;
40. 2-((4-Difluoromethoxy)dibenzo[b,d]furan-1-yl)-N-(2,2,2-trifluoroethyl)-1,3-thiazole-4-carboxamide;
41. 2-(4-Methoxydibenzo[b,d]furan-1-yl)-N-(2,2,2-trifluoroethyl)-1,3-thiazole-4-carboxamide;
42. 2-((4-Difluoromethoxy)dibenzo[b,d]furan-1-yl)-N-methoxy-1,3-thiazole-4-carboxamide;
43. 2-[4-(Difluoromethoxy)-8-(trifluoromethyl)dibenzo[b,d]furan-1-yl]-1,3-thiazole-4-carboxylic acid;
44. 2-(4-(Difluoromethoxy)-8-(trifluoromethyl)dibenzo[b,d]furan-1-yl)-N-(4-hydroxycyclohexyl)-1,3-thiazole-4-carboxamide;
45. (2-(4-(Difluoromethoxy)-8-(trifluoromethyl)dibenzo[b,d]furan-1-yl)-1,3-thiazol-4-yl)(4-hydroxypiperidin-1-yl)methanone;
46. 2-(4-(Difluoromethoxy)-(methylsulfonamido)dibenzo[b,d]furan-1-yl)-N-(4-hydroxycyclohexyl)-1,3-thiazole-4-carboxamide;
47. Ethyl-2-(4-(difluoromethoxy)-8-nitrodibenzo[b,d]furan-1-yl)-1,3-oxazole-4-carboxylate;
48. Ethyl-2-(4-(difluoromethoxy)-8-(methylsulfonamido)dibenzo[b,d]furan-1-yl)-1,3-oxazole-4-carboxylate;
49. 2-(4-(Difluoromethoxy)-8-(methylsulfonamido)dibenzo[b,d]furan-1-yl)-1,3-oxazole-4-carboxylic acid;

50. 2-(4-(Difluoromethoxy)-8-(methylsulfonamido)dibenzo[b,d]furan-1-yl)-N-(4-hydroxycyclohexyl)-1,3-oxazole-4-carboxamide;
51. N-Cyclopropyl-2-(4-(difluoromethoxy)-8-[(methylsulfonyl)amino]dibenzo[b,d]furan-1-yl)-1,3-oxazole-4-carboxamide;
52. N-Cyclopentyl-2-(4-(difluoromethoxy)-8-methylsulfonamido)dibenzo[b,d]furan-1-yl)-1,3-oxazole-4-carboxamide;
53. Ethyl 2-(4-methoxydibenzo[b,d]furan-1-yl)-5-methyl-1,3-oxazole-4-carboxylate;
54. 2-(4-Methoxydibenzo[b,d]furan-1-yl)-5-methyl-1,3-oxazole-4-carboxylic acid;
55. N-(3,5-Dichloropyridin-4-yl)-2-(4-methoxydibenzo[b,d]furan-1-yl)-5-methyl-1,3-oxazole-4-carboxamide;
56. N-Cyclopropyl-2-(4-methoxydibenzo[b,d]furan-1-yl)-5-methyl-1,3-oxazole-4-carboxamide;
57. N-Ethyl 2-(4-methoxydibenzo[b,d]furan-1-yl)-5-methyl-1,3-oxazole-4-carboxamide;
58. 2-(4-Methoxydibenzo[b,d]furan-1-yl)-5-methyl-1,3-oxazole-4-carboxamide;
59. N-Cyclopentyl-2-(4-methoxydibenzo[b,d]furan-1-yl)-5-methyl-1,3-oxazole-4-carboxamide;
60. N-(4-Hydroxycyclohexyl)-2-(4-methoxydibenzo[b,d]furan-1-yl)-5-methyl-1,3-oxazole-4-Carboxamide;
61. 2-(4-Methoxydibenzo[b,d]furan-1-yl)-5-methyl-N-(propan-2-yl)-1,3-oxazole-4-carboxamide;
62. Ethyl 2-(4-methoxydibenzo[b,d]furan-1-yl)-1,3-oxazole-4-carboxylate;
63. 2-(4-Methoxydibenzo[b,d]furan-1-yl)-1,3-oxazole-4-carboxylic acid;
64. Ethyl 2-(4-(2-(4-methoxydibenzo[b,d]furan-1-yl)-1,3-oxazole-4-carbonyl)piperazin-1-yl)pyrimidine-5-carboxylate;
65. N-(3,5-Dichloropyridin-4-yl)-2-(4-methoxydibenzo[b,d]furan-1-yl)-1,3-oxazole-4-carboxamide;
66. 2-(4-(2-(4-Methoxydibenzo[b,d]furan-1-yl)oxazole-4-carbonyl)piperazin-1-yl)pyrimidine-5-carboxylic acid;
67. 2-(4-Methoxydibenzo[b,d]furan-1-yl)-1,3-oxazole-4-carboxamide;
68. [2-(4-Methoxydibenzo[b,d]furan-1-yl)-1,3-oxazol-4-yl](4-(pyrimidin-2-yl)piperazin-1-yl)methanone;
69. 2-(4-Methoxydibenzo[b,d]furan-1-yl)-N-methyl-1,3-oxazole-4-carboxamide;
70. N-Cyclopropyl-2-(4-methoxydibenzo[b,d]furan-1-yl)-1,3-oxazole-4-carboxamide;
71. [2-(4-Methoxydibenzo[b,d]furan-1-yl)-1,3-oxazol-4-yl](pyrrolidin-1-yl)methanone;
72. 2-(4-Methoxydibenzo[b,d]furan-1-yl)-1,3-benzo[d]oxazole-5-carboxylic acid;
73. 2-(4-Methoxydibenzo[b,d]furan-1-yl)-1,3-benzo[d]oxazole-5-carboxamide;
74. 2-(4-Methoxydibenzo[b,d]furan-1-yl)-1,3-benzo[d]oxazole;
75. 2-(4-Methoxydibenzo[b,d]furan-1-yl)[1,3]oxazolo[4,5-b]pyridine;
76. N-Cyclopentyl-2-(4-methoxydibenzo[b,d]furan-1-yl)-1,3-benzo[d]oxazole-5-carboxamide; and
77. N-(4-Hydroxycyclohexyl)-2-(4-methoxydibenzo[b,d]furan-1-yl)-1,3-benzo[d]oxazole-5-carboxamide.

Described below is a process for the preparation of compounds of formula (I) as shown in the scheme 1.

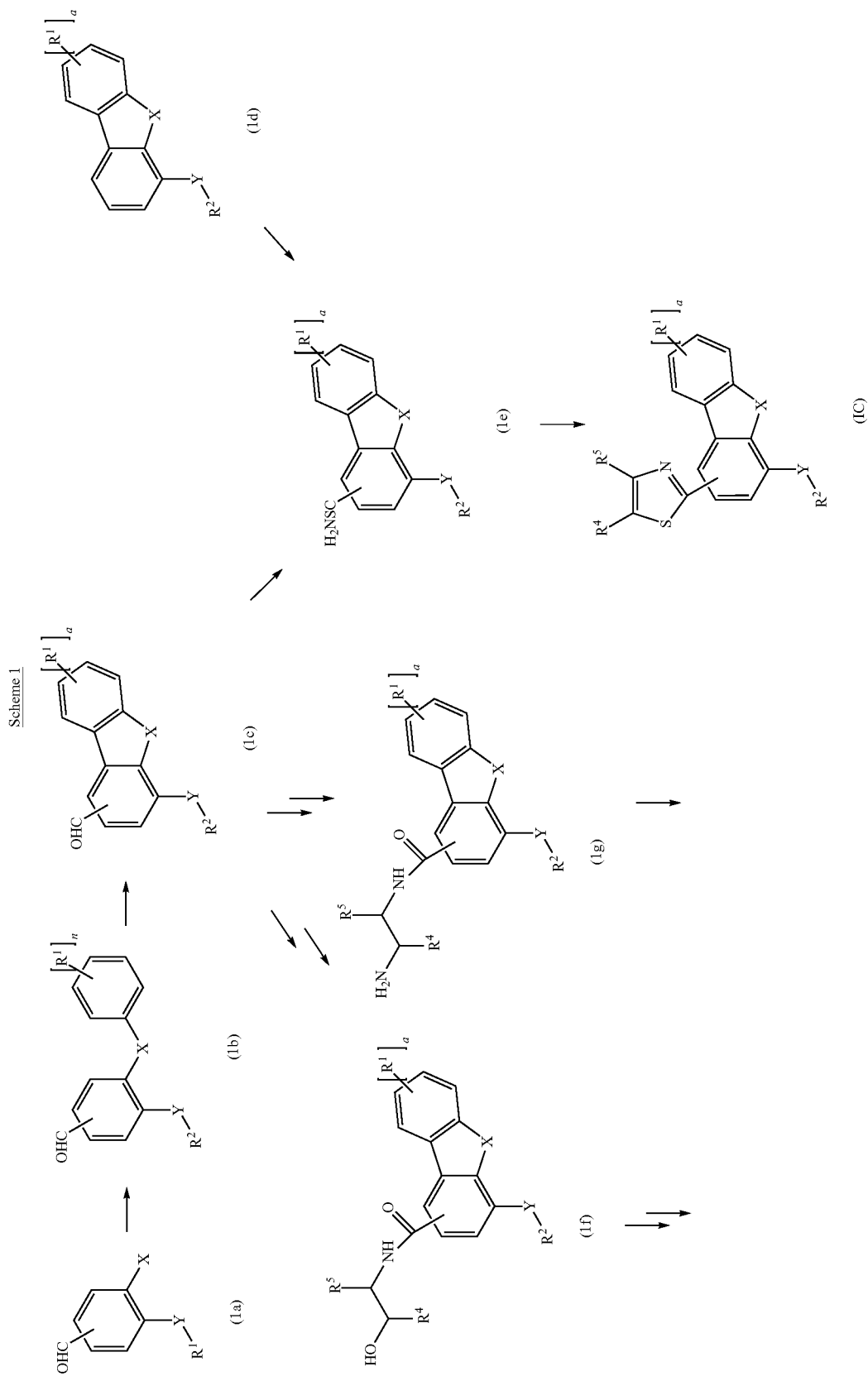

-continued
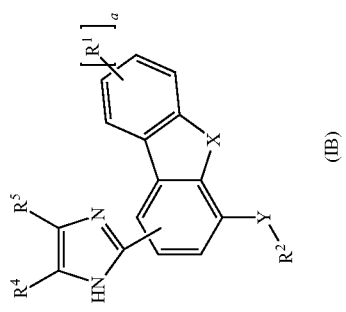
(IB)
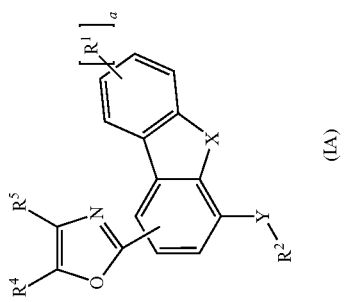
(IA)

The compound of formula (1a) is reacted with a suitably substituted aryl halide (preferably bromide or iodide) in suitable solvents such as acetonitrile, DMF, DMSO, tetrahydrofuran, dioxane, halogenated solvents such as 1,2-dichloroethane, in presence of a suitable non-nucleophilic bases which include KF, Na$_2$CO$_3$, Cs$_2$CO$_3$ at reflux temperatures and reaction time ranging from 1 hour to 48 hours followed by the isolation of the required product (1b) by the usual procedures. The compound of formula (1b) is cyclised, employing metal catalysts (palladium acetate in DMF, DMA or glacial acetic acid, nickel catalyst in pyridine or DMF, tetrakistriphenylphosphinepalladium in DMF and the like), preferably palladium acetate in DMF, to give the compound of formula (1c).

The compound of formula (1c) is oxidized to the acid through known literature procedures (such as sodium chlorite or potassium permanganate and the like). The acid intermediate is then converted to the corresponding amide. The amide on dehydration using dehydrating agents such as thionyl chloride or trifluoroactic anhydride (TFAA) or by direct dehydration of the oxime derivative of compound of formula (1c) using dehydrating agent such as thionyl chloride, TFAA and the like gives cyano compound. The cyano compound on reacting with P$_4$S$_{10}$ or Lawesson's reagent gives compound of formula (1e).

Alternatively, the compound of formula (1d) is reacted with metal thiocyanate such as potassium thiocyanate in solvents such as acetonitrile, DMF, DMSO, tetrahydrofuran, dioxane, halogenated solvents such as 1,2-dichloroethane, ethers such as 1,2-dimethoxyethane, water, alkyl or haloalkyl sulfonic acids like methane sulfonic acid, trifluoromethane sulfonic acid and the like or a mixture thereof at temperatures ranging from 0° C. to reflux temperatures and reaction time ranging from 1 hour to 48 hours followed by the isolation of the required product (1e) by the usual procedures.

The compound of formula (1e) is then converted to the compounds of formula (IC) by reacting the thioamide compound of formula (1e) with the optionally substituted bromo pyurvates.

The compound of formula (1c) is oxidized to the acid through known literature procedures (such as sodium chlorite or potassium permanganate and the like). The acid is then coupled with the optionally substituted amino acid featuring a hydroxyl group under appropriate basic conditions (EDC, or triethylamine or HBTU (2-(1H-Benzotriazol-1-yl)-1,1,3,3-tetramethyluroniumhexafluorophosphate), HOBt, diisopropylamine or triethylamine and the like) reported in the literature. The amide derivative (10 is then cyclized to oxazoline through literature known methods (DAST, Deoxo-flour, triphenyl phosphine, (CBrCl$_2$)$_2$ and the like). The oxazoline is then subjected to dehydrogenation, (methods include MnO$_2$, DBU:CCl$_4$:Pyridine, DDQ (2,3-Dichloro-5,6-Dicyano benzoquinone), chloranil and the like) to give the oxazole compound of formula (IA).

The compound of formula (1c) is oxidized to the acid through known literature procedures (such as sodium chlorite or potassium permanganate and the like). The acid is then coupled with the optionally substituted diamino compound under appropriate basic conditions (EDC, or triethylamine or HBTU, HOBt, diisopropylamine or triethylamine and the like) reported in the literature, followed by cyclization under acidic conditions gives (IB).

The examples given below are provided by the way of illustration only and therefore should not be construed to limit the scope of the invention.

REPRESENTATIVE EXPERIMENTAL PROCEDURES

Example 1

Synthesis of ethyl 6-(2-(4-methoxydibenzo[b,d]furan-1-yl)thiazol-4-yl)picolinate

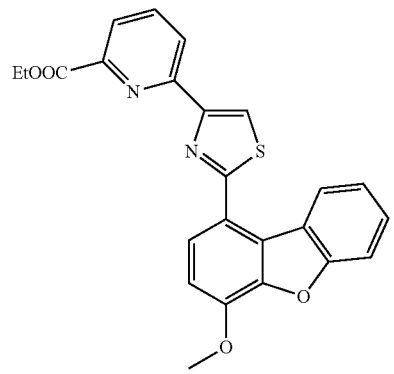 [SMILES: CCOC(=O)c1cccc(-c2csc(-c3ccc(OC)c4oc5ccccc5c34)n2)n1]

Step 1: Preparation of 4-methoxydibenzo[b,d]furan

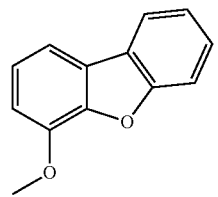

To a solution of 4-hydroxydibenzo[b,d]furan (2 g, 0.0109 mol) in DMF (5 mL) potassium carbonate (3.2 g, 0.0232 mol) and methyl iodide (1.35 mL, 0.0217 mol) was added. The reaction slurry was stirred at room temperature for 3 h. Subsequently the reaction mixture was poured into the cold water (100 mL) and extracted with hexane (3×100 mL). The organic layer was dried over anhydrous sodium sulphate and filtered.

The filtrate was evaporated at reduced pressure to, give the desired product in 66% yield, $R_f$ 0.74 (Ethyl acetate:Hexane (3:7); MS m/z: 199.1 (M+1).

Step 2: Preparation of 4-methoxydibenzo[b,d]furan-1-carbothioamide

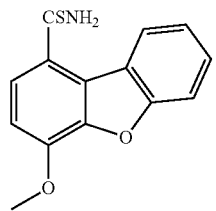

To a mixture of 4-methoxydibenzo[b,d]furan (1 g, 5.05 mmol) in methane sulphonic acid (11 mL), potassium thiocyanate (1 g, 10.29 mmol) was added at 0-5° C. Subsequently the reaction mass was stirred at room temperature for 3 h. The reaction mixture was poured into crushed ice and filtered. The solid was washed with hexane and dried, to furnish the required product in 70% yield; $R_f$ 0.25 (Ethyl acetate:Hexane (3:7); HPLC (purity); $^1$H-NMR (CDCl$_3$) δ: 4.08 (s, 3H), 6.97 (d, 1H), 7.26-7.30 (m, 1H), 7.33-7.37 (m, 1H), 7.65 (d, 1H), 7.69 (d, 1H), 7.94 (d, 1H), 8.31 (d, 1H); 91.4%; MS m/z: 258.1 (M+1).

Step 3: Preparation of ethyl 6-(2-(4-methoxydibenzo[b,d]furan-1-yl)thiazol-4-yl)picolinate To a stirred solution of 4-methoxydibenzo[b,d]furan-1-carbothioamide (140 mg, 0.544 mmol) in ethanol (5 mL) was added sodium bicarbonate (60 mg, 0.714 mmol) and ethyl 6-(2-bromoacetyl)picolinate (150 mg, 0.551 mmol). The stirring was continued at room temperature for 20 hours. The reaction mixture was poured into the water (25 mL) and extracted with ethyl acetate (2×25 mL). The organic layer was dried over anhydrous sodium sulphate and filtered. The filtrate was evaporated at reduced pressure to give the product, which was purified by column chromatography by using a gradient of ethyl acetate in hexane (0-6%). Yield—28%; $R_f$ 0.5 (Ethyl acetate:Hexane (3:7); HPLC (purity): 98.1%; $^1$H-NMR (CDCl$_3$) δ: 1.48-1.57 (m, 3H), 4.14 (s, 3H), 4.50-4.55 (m, 2H), 7.07 (d, 1H), 7.49-7.53 (m, 1H), 7.65-7.69 (m, 2H), 7.94-7.98 (m, 1H), 8.09 (d, 1H), 8.42 (s, 1H), 8.47 (d, 1H), 8.73 (d, 1H); MS m/z: 431.1 (M+1).

Example 2

Synthesis of 6-(2-(4-methoxydibenzo[b,d]furan-1-yl)thiazol-4-yl)picolinic acid

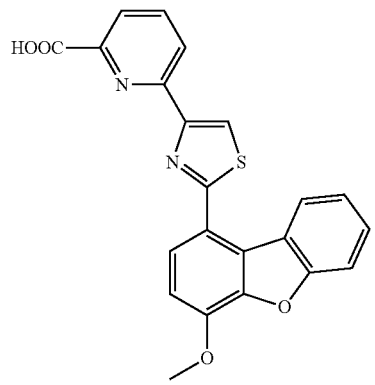 [SMILES: COc1ccc(-c2nc(-c3cccc(C(=O)O)n3)cs2)c2c1oc1ccccc12]

To a slurry of ethyl 6-(2-(4-methoxydibenzo[b,d]furan-1-yl)thiazol-4-yl)picolinate (50 mg, 0.116 mmol) in ethanol (5 mL), potassium hydroxide (30 mg, 0.535 mmol) in water (0.5 mL) was added. The reaction slurry was stirred at room temperature for 2 h. Subsequently the reaction mixture was poured into water acidified with 1N HCl to a pH of 3-4; the precipitated solid was filtered and washed with ether and hexane. Yield—42%; $R_f$ 0.23 (Chloroform:Methanol (8.5:1.5); HPLC (purity): 96%; $^1$H-NMR (CDCl$_3$) δ: 4.15 (s, 3H), 7.09 (d, 1H), 7.29-7.32 (m, 1H), 7.51-7.55 (m, 2H), 8.08-8.12 (m, 1H), 8.24 (d, 1H), 8.56 (d, 1H), 8.75 (d, 1H); MS m/z: 403.1 (M+1).

The following compounds were, prepared according to the procedure outlined above.

| Ex. No | Analytical Data | Structure |
|---|---|---|
| 3 | $^1$H-NMR (CDCl$_3$) δ: 1.58-1.63 (m, 6H), 4.36-4.42 (m, 2H), 4.50-4.55 (m, 2H), 7.06 (d, 1H), 7.26-7.30 (m, 1H), 7.48-7.52 (m, 1H), 7.62-7.70 (m, 2H), 7.93-7.97 (m, 1H), 8.09 (d, 1H), 8.41 (s, 1H), 8.47 (d, 1H), 8.72 (d, 1H); MS m/z: 445.0 (M + 1). | 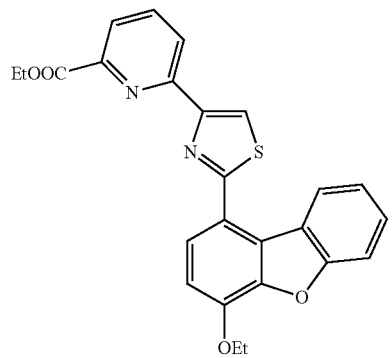 [SMILES: CCOc1ccc(-c2nc(-c3cccc(C(=O)O)n3)cs2)c2c1oc1ccccc12] |

-continued

| Ex. No | Analytical Data | Structure |
|---|---|---|
| 4 | ¹H-NMR (DMSO-d$_6$) δ: 1.48-1.52 (m, 3H), 4.35-4.40 (m, 2H), 7.34 (d, 1H), 7.40-7.43 (m, 1H), 7.58-7.62 (m, 1H), 7.79-7.84 (m, 2H), 8.05 (d, 1H), 8.15-8.19 (m, 1H), 8.36 (d, 1H), 8.65 (s, 1H), 8.94 (d, 1H); MS m/z: 417.0 (M + 1). | 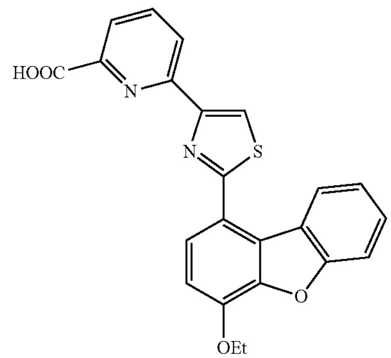 |
| 5 | ¹H-NMR (CDCl$_3$) δ: 1.41-1.45 (m, 3H), 4.43-4.48 (m, 2H), 6.67-7.03 (m, 1H), 7.22-7.26 (m, 2H), 7.31 (d, 1H), 7.46-7.50 (m, 1H), 7.59-7.62 (m, 2H), 7.88-7.91 (m, 1H), 8.04 (d, 1H), 8.37-8.41 (m, 1H), 8.60 (d, 1H); MS m/z: 466.9 (M + 1). | 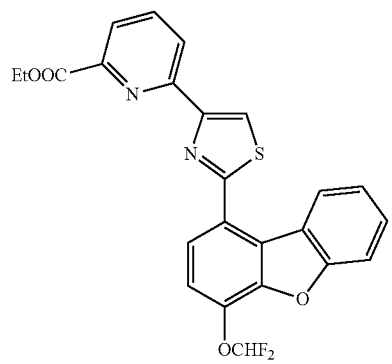 [SMILES: CCOC(=O)c1cccc(-c2csc(-c3ccc(OC(F)F)c4oc5ccccc5c34)n2)n1] |
| 6 | ¹H-NMR (DMSO-d$_6$) δ: 7.45-7.48 (m, 1H), 7.59 (d, 2H), 7.64-7.68 (m, 1H), 7.87-7.91 (m, 2H), 8.07 (d, 1H), 8.16-8.20 (m, 1H), 8.37 (d, 1H), 8.75 (s, 1H), 8.89 (s, 1H); MS m/z: 438.9 (M + 1). | 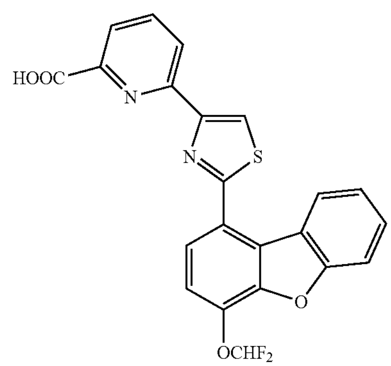 [SMILES: O=C(O)c1cccc(-c2csc(-c3ccc(OC(F)F)c4oc5ccccc5c34)n2)n1] |
| 7 | ¹H-NMR (CDCl$_3$) δ: 4.06 (s, 3H), 4.22 (s, 3H), 7.21 (d, 1H), 7.36-7.41 (m, 1H), 7.53 (d, 1H), 7.67-7.70 (m, 1H), 7.96 (d, 1H), 8.03-8.06 (m, 1H), 8.22 (d, 1H), 8.37-8.40 (m, 1H), 8.59 (s, 1H); MS m/z: 432.3 (M + 1). | 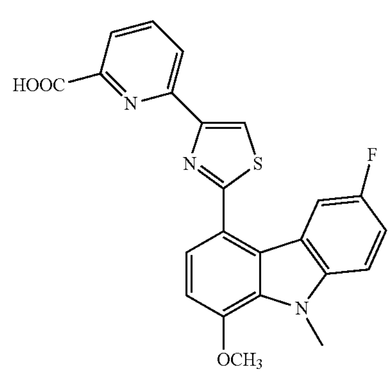 [SMILES: COc1ccc(-c2nc(-c3cccc(C(=O)O)n3)cs2)c2c3cc(F)ccc3n(C)c12] |

-continued
| Ex. No | Analytical Data | Structure |
|---|---|---|
| 8 | $^1$H-NMR (CDCl$_3$) δ: 4.15 (s, 3H), 7.07 (d, 1H), 7.30 (d, 1H), 7.51-7.55 (m, 1H), 7.64-7.70 (m, 2H), 7.76-7.81 (m, 3H), 8.19 (d, 2H), 8.72 (d, 1H); MS m/z-383.1 (M + 1). | 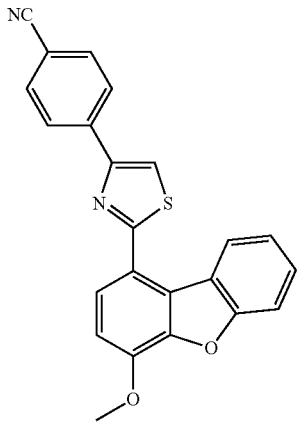 [SMILES: COc1ccc(-c2nc(-c3ccc(C#N)cc3)cs2)c2c1oc1ccccc12] |
| 9 | $^1$H-NMR (DMSO-d$_6$) δ: 4.14 (s, 3H), 7.45-7.48 (m, 1H), 7.58-7.62 (m, 1H), 7.79 (d, 1H), 7.85 (d, 1H), 8.05 (d, 1H), 8.15-8.19 (m, 1H), 8.31-8.33 (d, 1H), 8.45 (s, 1H), 8.50-5.52 (m, 1H), 8.58 (s, 1H); MS m/z: 403.2 (M + 1). | 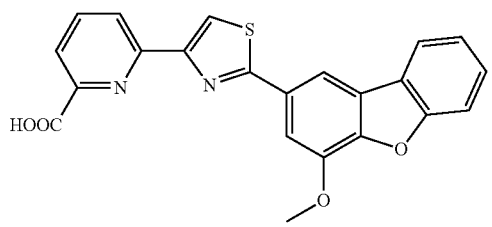 [SMILES: COc1cc(-c2nc(-c3cccc(C(=O)O)n3)cs2)cc2c1oc1ccccc12] |
| 10 | $^1$H-NMR (DMSO-d$_6$) δ: 3.05 (s, 3H), 4.14 (s, 3H), 7.41 (d, 1H), 7.77 (d, 1H), 7.86 (s, 1H), 8.07 (d, 1H), 8.13-8.19 (m, 2H), 8.45 (s, 1H), 8.52 (d, 1H), 8.60 (s, 1H), 9.84 (s, 1H); MS m/z: 494.0 (M + 1). | 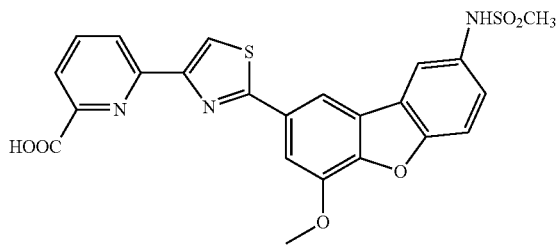 |
| 11 | $^1$H-NMR (CDCl$_3$) δ: 2.99-3.02 (m, 2H), 3.38-3.4 (m, 2H), 4.10 (s, 3H), 7.04-7.15 (m, 3H), 7.54-7.57 (m, 2H), 8.29-8.34 (m, 3H); MS m/z: 498.0 (M + 1). | 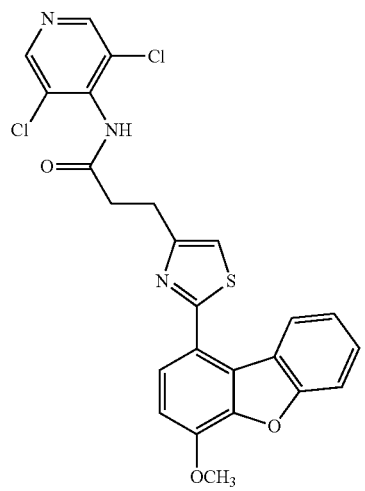 [SMILES: COc1ccc(-c2nc(CCC(=O)Nc3c(Cl)cncc3Cl)cs2)c2c1oc1ccccc12] |

-continued
| Ex. No | Analytical Data | Structure |
|---|---|---|
| 12 | ¹H-NMR (CDCl₃) δ: 4.14 (d, 5H), 7.06 (d, 1H), 7.19-7.23 (m, 1H), 7.32 (s, 1H), 7.45-7.49 (m, 1H), 7.60 (d, 1H), 7.65 (d, 1H), 8.38 (s, 2H), 8.51 (d, 1H), 9.50 (s, 1H); Mass m/z: 484.0 (M + 1) | 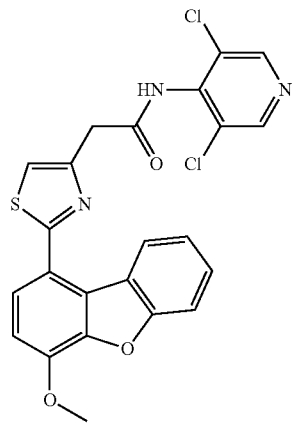 [SMILES: COc1ccc(-c2nc(CC(=O)Nc3c(Cl)cncc3Cl)cs2)c2c1oc1ccccc12] |
| 13 | ¹H-NMR (CDCl₃) δ: 4.14 (d, 3H), 7.09 (d, 1H), 7.27-7.34 (m, 1H), 7.49-7.55 (m, 1H), 7.61 (d, 1H), 7.81 (d, 1H), 8.41 (s, 1H), 8.48 (d, 1H), 8.61 (d, 2H), 9.17 (s, 1H); Mass m/z : 470.0 (M + 1) | 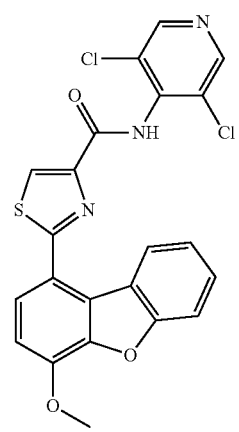 [SMILES: COc1ccc(-c2nc(C(=O)Nc3c(Cl)cncc3Cl)cs2)c2c1oc1ccccc12] |
| 14 | ¹H-NMR (CDCl₃) δ: 6.75, 6.93, 7.11 (brs, 1H), 7.30-7.34 (m, 1H), 7.41 (d, 1H), 7.55-7.61 (m, 2H), 7.66-7.71 (m, 1H), 8.44 (d, 1H), 8.48 (s, 1H), 8.60 (s, 2H), 9.14 (s, 1H); Mass m/z: 505.9 (M + 1). | 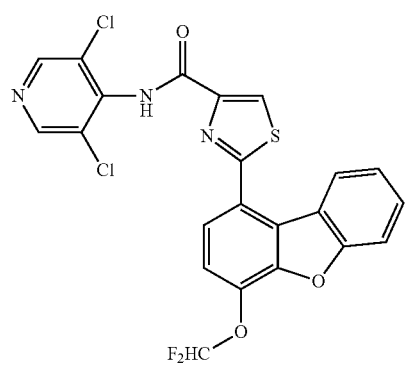 [SMILES: O=C(Nc1c(Cl)cncc1Cl)c1csc(-c2ccc(OC(F)F)c3oc4ccccc4c23)n1] |
| 15 | ¹H-NMR (CDCl₃) δ: 1.50-1.53 (m, 3H), 4.13 (s, 3H), 4.48-4.53 (m, 2H), 7.04 (d, 1H), 7.35-7.39 (m, 1H), 7.50-7.55 (m, 1H), 7.65-7.69 (m, 2H), 8.24 (s, 1H), 9.21 (s, 1H); Mass m/z: 354.1 (M + 1). | 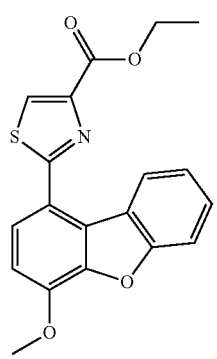 [SMILES: CCOC(=O)c1csc(-c2ccc(OC)c3oc4ccccc4c23)n1] |

| Ex. No | Analytical Data | Structure |
|---|---|---|
| 16 | $^1$H-NMR (DMSO-$d_6$) δ: 4.08 (s, 3H), 7.33-7.39 (m, 2H), 7.58-7.62 (m, 1H), 7.78 (d, 1H), 7.85 (d, 1H), 8.58 (s, 1H), 9.27 (d, 1H); Mass m/z: 326.0 (M + 1). | 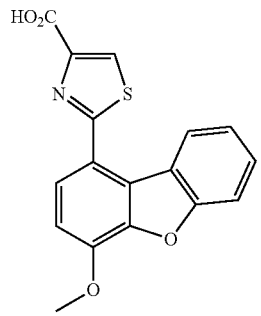 [SMILES: COc1ccc(-c2nc(C(=O)O)cs2)c2c1oc1ccccc12] |
| 17 | $^1$H-NMR (CDCl$_3$) δ: 4.16 (d, 3H), 7.09 (d, 1H), 7.14-7.18 (m, 1H), 7.31-7.37 (m, 1H), 7.40 (d, 2H), 7.53-7.57 (m, 1H), 7.62 (d, 1H), 7.71-7.74 (m, 3H), 8.32 (s, 1H), 8.52 (d, 1H), 9.39 (s, 1H); Mass m/z: 401.1 (M + 1). | 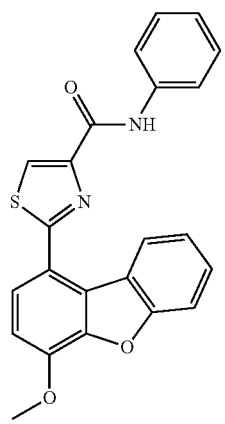 [SMILES: COc1ccc(-c2nc(C(=O)Nc3ccccc3)cs2)c2c1oc1ccccc12] |
| 18 | $^1$H-NMR (DMSO-$d_6$) δ: 3.82-3.86 (m, 8H), 4.08 (s, 3H), 6.67 (d, 1H), 7.34-7.38 (m, 2H), 7.58 (d, 1H), 7.78 (d, 1H), 7.83 (d, 1H), 8.30 (s, 1H), 8.37 (d, 2H), 8.87 (d, 1H); Mass m/z: 472.1 (M + 1). | 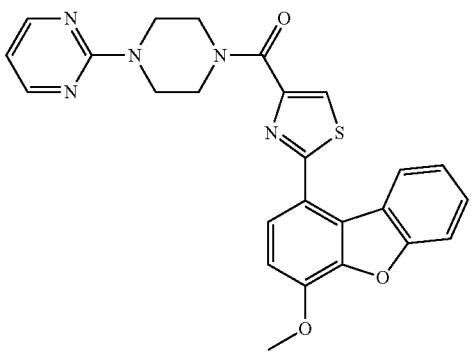 [SMILES: COc1ccc(-c2nc(C(=O)N3CCN(c4ncccn4)CC3)cs2)c2c1oc1ccccc12] |
| 19 | $^1$H-NMR (DMSO-$d_6$) δ: 3.54 (s, 2H), 3.66 (d, 2H), 3.86 (d, 4H), 4.08 (s, 3H), 6.65-6.68 (m, 1H), 6.84 (s, 1H), 7.34-7.39 (m, 2H), 7.52-7.60 (m, 2H), 7.77-7.84 (m, 2H), 8.11 (d, 1H), 8.30 (s, 1H), 8.88 (d, 1H); Mass m/z: 471.1 (M + 1). | 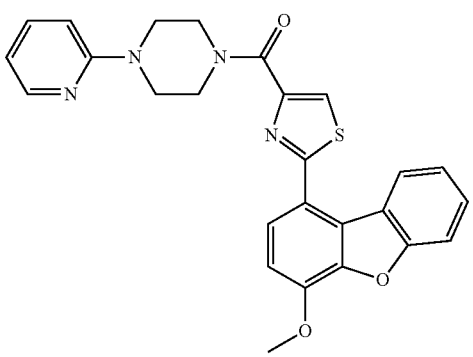 |

-continued
| Ex. No | Analytical Data | Structure |
|---|---|---|
| 20 | $^1$H-NMR (CDCl3) δ 4.16 (s, 3H), 7.09 (d, 1H), 7.30 (d, 3H), 7.34 (d, 1H), 7.53-7.57 (m, 1H), 7.61 (d, 2H), 7.66-7.73 (m, 1H), 8.32 (s, 1H), 8.47 (d, 1H), 9.39 (s, 1H); Mass m/z: 435.0 (M + 1). | 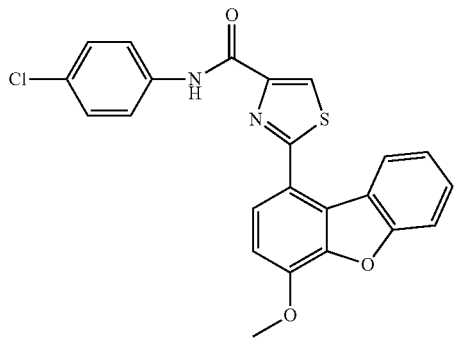 [SMILES: COc1ccc(-c2nc(C(=O)Nc3ccc(Cl)cc3)cs2)c2c1oc1ccccc12] |
| 21 | $^1$H-NMR (CDCl3) δ: 1.39-1.44 (m, 3H), 2.92 (s, 3H), 4.13 (s, 3H), 4.37-4.42 (m, 2H), 7.04 (d, 1H), 7.32-7.36 (m, 1H), 7.50-7.54 (m, 1H), 7.65 (d, 2H), 8.78 (d, 1H); Mass m/z: 368.1 (M + 1). | 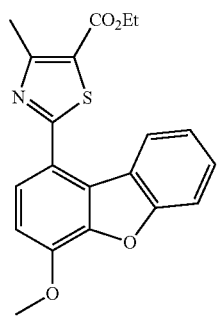 [SMILES: CCOC(=O)c1sc(-c2ccc(OC)c3oc4ccccc4c23)nc1C] |
| 22 | $^1$H-NMR (CDCl3) δ: 3.88 (s, 3H), 4.13 (s, 3H), 7.00-7.06 (m, 3H), 7.28-7.32 (m, 1H), 7.46-7.52 (m, 2H), 7.63-7.67 (m, 2H), 8.02 (d, 2H), 8.83 (d, 1H); Mass m/z: 388.1 (M + 1). | 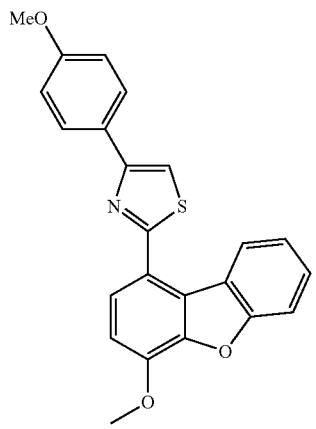 [SMILES: COc1ccc(-c2csc(-c3ccc(OC)c4oc5ccccc5c34)n2)cc1] |
| 23 | $^1$H-NMR (DMSO-d$_6$) δ: 2.82 (s, 3H), 4.08 (s, 3H), 7.32 (d, 1H), 7.41 (s, 1H), 7.60 (s, 1H), 7.77-7.83 (m, 2H), 8.90 (d, 1H); Mass m/z: 340.1 (M + 1). | 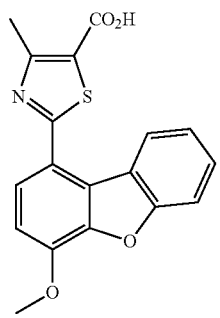 |

-continued
| Ex. No | Analytical Data | Structure |
|---|---|---|
| 24 | ¹H-NMR (CDCl₃) δ: 2.98 (s, 3H), 4.15 (s, 3H), 7.07 (d, 1H), 7.37 (s, 1H), 7.47 (s, 1H), 7.54 (d, 1H), 7.67-7.69 (m, 2H), 8.60 (s, 2H), 8.82 (d, 1H); Mass m/z: 484.0 (M + 1). | 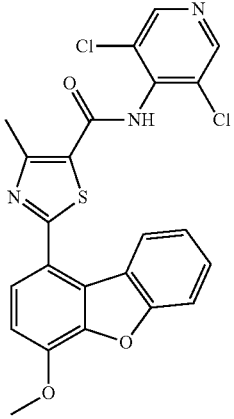 [SMILES: COc1ccc(-c2nc(C)c(C(=O)Nc3c(Cl)cncc3Cl)s2)c2c1oc1ccccc12] |
| 25 | ¹H-NMR (DMSO-d₆) δ: 4.08 (s, 3H), 7.32-7.37 (m, 2H), 7.59 (s, 1H), 7.73-7.80 (m, 4H), 8.43 (s, 1H), 8.61 (s, 1H); Mass m/z: 325.0 (M + 1). | 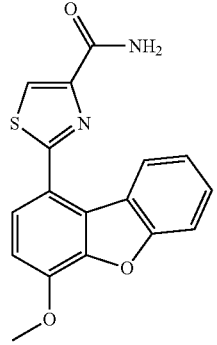 [SMILES: COc1ccc(-c2nc(C(N)=O)cs2)c2c1oc1ccccc12] |
| 26 | ¹H-NMR (CDCl₃) δ: 1.51-1.54 (m, 2H), 1.62-1.73 (m, 4H), 2.06-2.10 (m, 2H), 2.95 (s, 3H), 4.13 (s, 3H), 4.41-4.45 (m, 1H), 7.04 (d, 1H), 7.29 (d, 1H), 7.52-7.57 (m, 3H), 7.68 (d, 1H), 8.54 (d, 1H); Mass m/z: 407.1 (M + 1). | 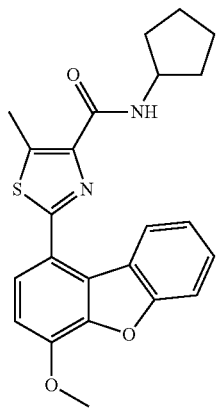 [SMILES: COc1ccc(-c2nc(C(=O)NC3CCCC3)c(C)s2)c2c1oc1ccccc12] |

| Ex. No | Analytical Data | Structure |
|---|---|---|
| 27 | ¹H-NMR (DMSO-d$_6$) δ: 1.34-1.42 (m, 4H), 1.83-1.90 (m, 4H), 2.83 (s, 3H), 3.42 (s, 1H), 3.78 (s, 1H), 4.08 (s, 3H), 4.57 (d, 1H), 7.30-7.35 (m, 2H), 7.58-7.62 (m, 1H), 7.67 (d, 1H), 7.78-7.85 (m, 2H), 8.62 (d, 1H); Mass m/z: 437.1 (M + 1). | 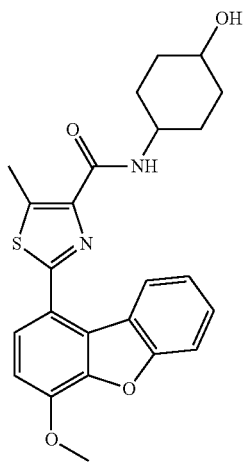 [SMILES: COc1ccc(-c2nc(C(=O)NC3CCC(O)CC3)c(C)s2)c2c1oc1ccccc12] |
| 28 | ¹H-NMR (DMSO-d$_6$) δ: 2.87 (s, 3H), 4.08 (s, 3H), 7.30-7.36 (m, 2H), 7.57-7.61 (m, 1H), 7.70 (d, 1H), 7.78 (d, 1H), 8.63 (d, 1H), 8.76 (s, 2H), 10.44 (s, 1H); Mass m/z: 484.0 (M + 1). | 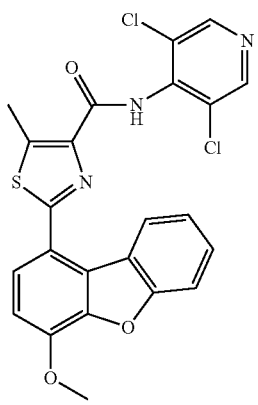 [SMILES: COc1ccc(-c2nc(C(=O)Nc3c(Cl)cncc3Cl)c(C)s2)c2c1oc1ccccc12] |
| 29 | ¹H-NMR (CDCl$_3$) δ: 1.17-1.21 (m, 3H), 2.88 (s, 3H), 3.39-3.46 (m, 2H), 4.06 (s, 3H), 6.97 (d, 1H), 7.19-7.23 (m, 1H), 7.42-7.49 (m, 3H), 7.61 (d, 1H), 8.39 (d, 1H); Mass m/z: 367.1 (M + 1). | 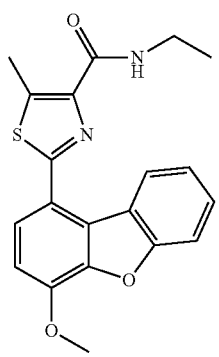 [SMILES: CCNC(=O)c1nc(-c2ccc(OC)c3oc4ccccc4c23)sc1C] |

| Ex. No | Analytical Data | Structure |
|---|---|---|
| 30 | ¹H-NMR (CDCl₃) δ: 2.98 (s, 4H), 3.90 (s, 4H), 4.14 (s, 3H), 7.07 (d, 1H), 7.29 (d, 1H), 7.52-7.60 (m, 2H), 7.70 (d, 1H), 8.23 (s, 1H), 8.28 (s, 1H), 8.45 (d, 1H); Mass m/z: 410.0 (M + 1). | 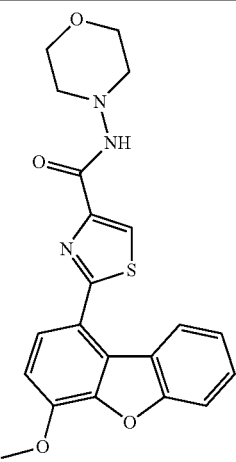 |
| 31 | ¹H-NMR (CDCl₃) δ: 1.41 (d, 4H), 2.03 (d, 2H), 2.15 (d, 2H), 3.41-3.47 (m, 1H), 3.82-3.85 (m, 1H), 4.14 (s, 3H), 7.07 (d, 1H), 7.24-7.28 (m, 1H), 7.35 (d, 1H), 7.51-7.55 (m, 1H), 7.59 (d, 1H), 7.69 (d, 1H), 8.19 (s, 1H), 8.46 (d, 1H); Mass m/z: 423.1 (M + 1). | 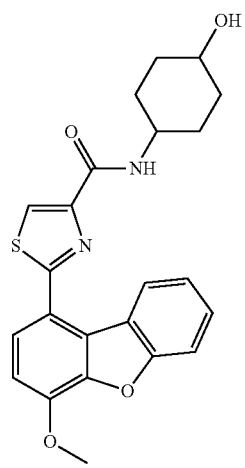 [SMILES: COc1ccc(-c2nc(C(=O)NC3CCC(O)CC3)cs2)c2c1oc1ccccc12] |
| 32 | ¹H-NMR (DMSO-d₆) δ: 2.85 (s, 3H), 7.41-7.59-7.77 (t, 1H), 7.67 (d, 1H), 7.95 (d, 1H), 8.10 (d, 1H), 8.51-8.54 (m, 1H), 10.30 (d, 1H), 13.30 (s, 1H); Mass m/z: 421.0 (M + 1). | 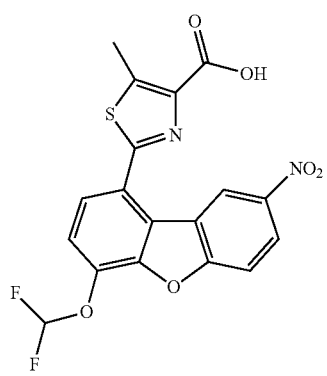 [SMILES: Cc1sc(-c2ccc(OC(F)F)c3oc4ccc([N+](=O)[O-])cc4c23)nc1C(=O)O] |

-continued
| Ex. No | Analytical Data | Structure |
|---|---|---|
| 33 | $^1$H-NMR (DMSO-d$_6$) δ: 2.84 (s, 3H), 2.97 (s, 3H), 7.37-7.56 (m, 3H), 7.74 (d, 1H), 7.83 (d, 1H), 8.74 (d, 1H), 9.61 (s, 1H), 13.14 (s, 1H); Mass m/z: 469.0 (M + 1). | 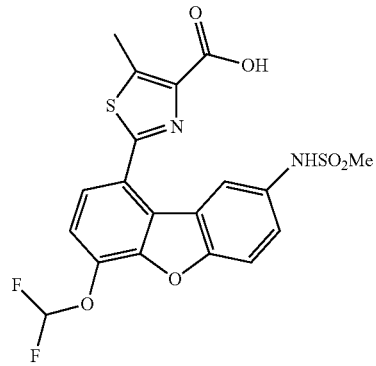 |
| 34 | $^1$H-NMR (DMSO-d$_6$) δ: 2.87 (s, 3H), 7.58-7.80 (m, 3H), 7.84 (d, 1H), 7.87 (s, 1H), 8.16 (d, 1H), 8.74 (s, 2H), 8.81 (s, 1H), 9.63 (s, 1H), 10.42 (s, 1H); Mass m/z: 599.1 (M + 1). | 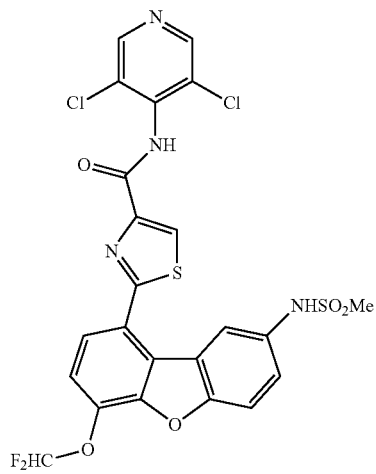 |
| 35 | $^1$H-NMR (DMSO-d$_6$) δ: 1.40 (d, 4H) 1.80-1.87 (m, 4H), 2.86 (s, 3H), 2.90 (s, 3H), 3.41-3.47 (m, 1H), 3.82-3.85 (m, 1H), 4.53 (d, 1H), 7.48-7.55 (m, 3H), 7.67-7.72 (m, 2H), 7.84 (d, 1H), 8.21 (d, 1H), 9.76 (s, 1H); Mass m/z: 566.0 (M + 1). | 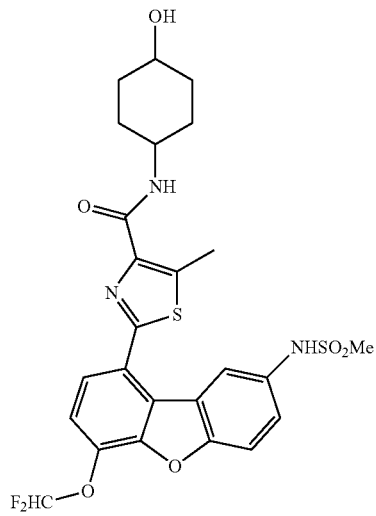 |

| Ex. No | Analytical Data | Structure |
|---|---|---|
| 36 | ¹H-NMR (DMSO-d$_6$) δ: 2.03 (s, 3H), 7.37-7.56 (m, 2H), 7.74-7.78 (m, 3H), 8.62 (s, 1H), 8.78 (s, 1H), 9.90 (s, 1H); Mass m/z: 417.0 (M + 1). | 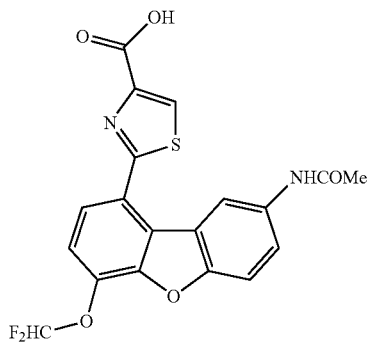 |
| 37 | ¹H-NMR (DMSO-d$_6$) δ: 2.87 (s, 3H), 2.94 (s, 3H), 3.70 (s, 3H), 7.37-7.73 (m, 4H), 7.83 (d, 1H), 8.23 (d, 1H), 9.76 (s, 1H), 11.48 (s, 1H); Mass m/z: 498.0 (M + 1). | 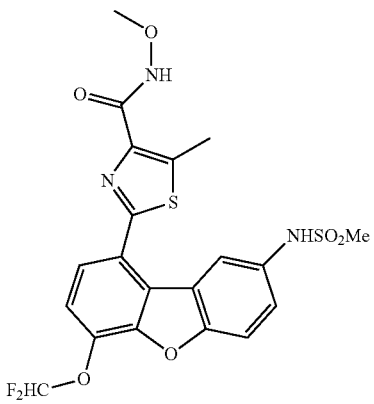 |
| 38 | ¹H-NMR (DMSO-d$_6$) δ: 1.23-1.31 (m, 2H) 1.40 (d, 2H), 1.78-1.88 (m, 4H), 2.05 (s, 3H), 3.39 (s, 1H), 3.82-3.85 (m, 1H), 4.57 (d, 1H), 7.37-7.73 (m, 2H), 7.74 (d, 2H), 7.76-7.80 (m, 2H), 8.50 (s, 1H), 8.69 (d, 1H), 10.12 (s, 1H), Mass m/z: 516.0 (M + 1). | 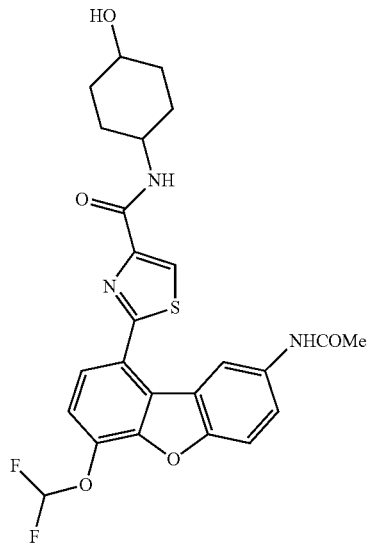 |

-continued

| Ex. No | Analytical Data | Structure |
|---|---|---|
| 39 | ¹H-NMR (CDCl₃) δ: 1.25-1.31 (m, 2H) 1.58-1.67 (m, 2H), 2.04 (d, 2H), 2.16 (d, 2H), 3.41-3.47 (m, 1H), 3.82-3.85 (m, 1H), 6.73-6.91-7.09 (t, 1H), 7.30 (d, 2H), 7.38 (d, 1H), 7.56-7.60 (m, 2H), 7.70 (d, 1H), 8.26 (s, 1H), 8.40 (d, 1H); Mass m/z: 459.0 (M + 1). | 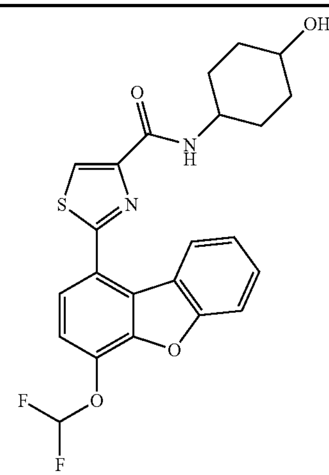 |
| 40 | ¹H-NMR (CDCl₃) δ: 4.14-4.17 (m, 2H), 6.74-6.92-7.10 (t, 1H), 7.31-7.35 (m, 1H), 7.39 (d, 1H), 7.56-7.61 (m, 2H), 7.68-7.73 (m, 2H), 8.36 (d, 2H); Mass m/z: 443.0 (M + 1). | 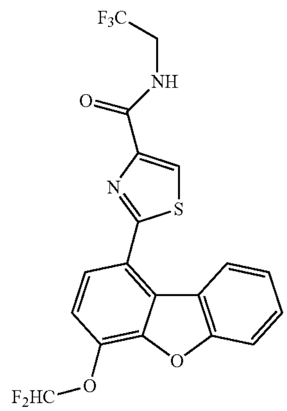 [SMILES: O=C(NCC(F)(F)F)c1csc(-c2ccc(OC(F)F)c3oc4ccccc4c23)n1] |
| 41 | ¹H-NMR (CDCl₃) δ: 4.13-4.17 (m, 5H), 7.07 (d, 1H), 7.30 (s, 1H), 7.53 (s, 1H), 7.59 (d, 1H), 7.69 (d, 1H), 7.73-7.81 (m, 1H), 8.28 (s, 1H), 8.42 (d, 1H); Mass m/z: 407.0 (M + 1). | 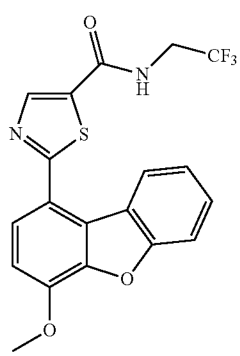 [SMILES: COc1ccc(-c2ncc(C(=O)NCC(F)(F)F)s2)c2c1oc1ccccc12] |
| 42 | ¹H-NMR (CDCl₃) δ: 3.95 (s, 3H), 6.74-6.92-7.10 (t, 1H), 7.33-7.39 (m, 2H), 7.55-7.60 (m, 2H), 7.69 (d, 1H), 8.28 (d, 1H), 8.37 (s, 1H), 9.77 (s, 1H); Mass m/z: 391.0 (M + 1). | 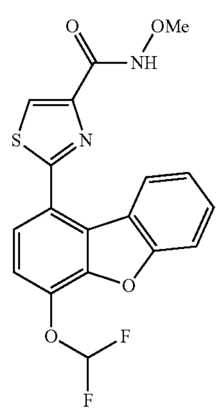 [SMILES: CONC(=O)c1csc(-c2ccc(OC(F)F)c3oc4ccccc4c23)n1] |

-continued
| Ex. No | Analytical Data | Structure |
|---|---|---|
| 43 | ¹H-NMR (DMSO-d₆) δ: 7.32-7.50-7.61 (t, 1H), 7.62 (d, 1H), 8.03 (s, 1H), 8.07-8.10 (m, 2H), 8.69 (s, 1H), 10.02 (s, 1H), 13.38 (s, 1H); Mass m/z: 430.0 (M + 1). | 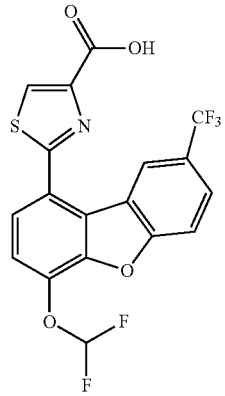 [SMILES: O=C(O)c1csc(-c2ccc(OC(F)F)c3oc4ccc(C(F)(F)F)cc4c23)n1] |
| 44 | ¹H-NMR (DMSO-d₆) δ: 1.25-1.31 (m, 2H), 1.36-1.42 (m, 2H), 1.84 (d, 4H), 3.41 (s, 1H), 3.77 (s, 1H), 4.57 (d, 1H), 7.42-7.61-7.79 (t, 1H), 7.66 (d, 1H), 7.92 (d, 1H), 8.02 (d, 1H), 8.07 (d, 1H), 8.12 (d, 1H), 8.52 (s, 1H), 9.06 (s, 1H); Mass m/z: 527.0 (M + 1). | 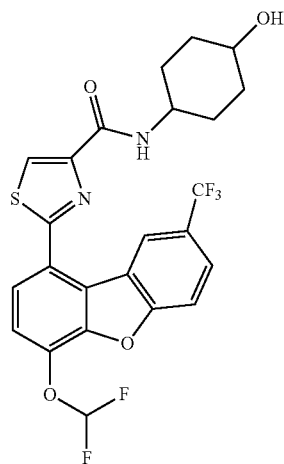 [SMILES: O=C(NC1CCC(O)CC1)c1csc(-c2ccc(OC(F)F)c3oc4ccc(C(F)(F)F)cc4c23)n1] |
| 45 | ¹H-NMR (CDCl₃) δ: 1.30 (s, 1H), 1.46 (s, 1H), 1.65 (s, 1H), 1.83 (s, 1H), 3.39 (d, 2H), 3.74 (s, 1H), 3.83 (s, 1H), 4.05 (s, 1H), 4.78 (d, 1H), 7.42-7.60-7.78 (t, 1H), 7.66 (d, 1H), 8.03 (d, 2H), 8.11 (d, 1H), 8.31 (s, 1H), 9.49 (s, 1H); Mass m/z: 513.0 (M + 1). | 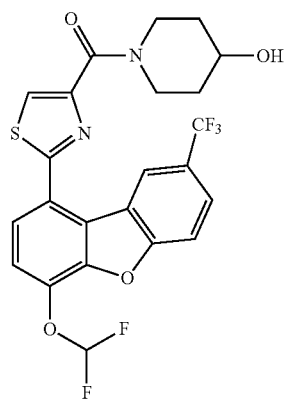 [SMILES: O=C(c1csc(-c2ccc(OC(F)F)c3oc4ccc(C(F)(F)F)cc4c23)n1)N1CCC(O)CC1] |

| Ex. No | Analytical Data | Structure |
|---|---|---|
| 46 | $^1$H-NMR (CDCl$_3$) δ: 1.25 (d, 2H), 1.46 (d, 2H), 1.84 (s, 4H), 2.91 (s, 3H), 3.39 (s, 1H), 3.74 (s, 1H), 4.54 (d, 1H), 7.49-7.57 (m, 3H), 7.77 (d, 1H), 7.81-7.86 (m, 2H), 8.22 (s, 1H), 8.51 (s, 1H), 9.74 (s, 1H); Mass m/z: 552.0 (M + 1). | 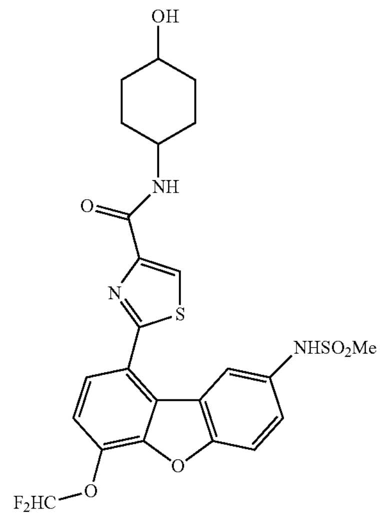 |

Example 47

Synthesis of ethyl 2-(4-(difluoromethoxy)-8-nitrodibenzo[b,d]furan-1-yl)-1,3-oxazole-4-carboxylate

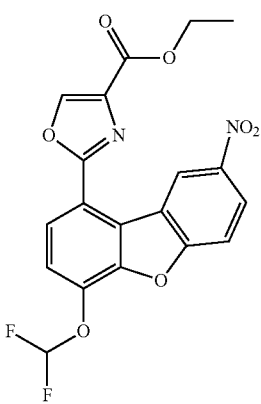 [SMILES: CCOC(=O)c1coc(-c2ccc(OC(F)F)c3oc4ccc([N+](=O)[O-])cc4c23)n1]

Step 1: Synthesis of 4-(difluoromethoxy)-3-hydroxy benzaldehyde

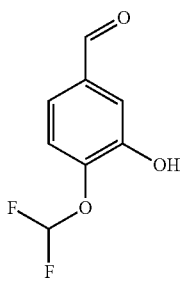

To a stirred solution of 3,4-dihydroxybenzaldehyde (25 g, 0.181 mol) in DMF (75 mL), potassium carbonate (70 g, 0.507 mol) was added. It was refluxed to 75-80° C. Chlorodifluoro methane gas was purged into the reaction mixture until 95% of the starting material was consumed. The reaction mixture was poured into the crushed ice and kept aside. After sometime the aqueous layer was extracted with ethyl acetate (3×500 mL). The organics were dried over sodium sulphate and filtered. The filtrate was evaporated under reduced pressure to give the crude product. The product was purified by column chromatography by using gradient (0-1) % of ethyl acetate in hexane. The solid obtained was washed with hexane and dried. Yield—25.3%. R$_f$—0.41 (Ethyl acetate:Hexane (3:7).

Step 2: Synthesis of 3-(2-bromo-4-nitrophenoxy)-4-(difluoromethoxy)benzaldehyde

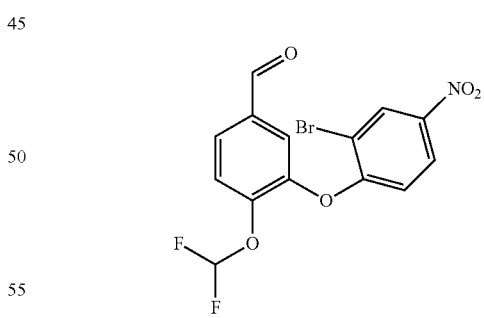

To a solution of 4-(difluoromethoxy)-3-hydroxy benzaldehyde (8.6 g, 0.046 mol) in dimethylsulphoxide (15 mL) was added potassium fluoride (5.36 g, 0.092 mol) at room temperature. Then it was refluxed to 100-120° C. To this 2-bromo-1-fluoro-4-nitrobenzene (20.3 g, 0.093 mol) in dimethylsulphoxide (10 mL) was added dropwise at 100-120° C. The heating was continued for 5 hours. The reaction mixture was poured into the crushed ice and stirred for 1 hour. Then the aqueous layer was decanted. The solid obtained was dissolved in ethyl acetate (500 mL). The organic layer was washed with water (3×200 mL). The organics were dried over sodium sulphate and filtered. The solvents were removed in vacuum to give the crude product. The product was purified by column chromatography by using gradient (0-2) % of ethyl acetate in hexane. The solid obtained was washed with hexane and dried. Yield—66%. $^1$H-NMR (DMSO-$d_6$) δ: 7.06 (d, 1H), 7.23-7.41-7.59 (t, 1H), 7.67 (d, 1H), 7.82 (d, 1H), 7.96-7.98 (m, 1H), 8.20-8.23 (m, 1H), 8.61 (d, 1H), 9.97 (s, 1H); HPLC (purity): 99.5%; Mass calculated for $C_{14}H_8BrF_2NO_5$-388.1, observed—388.1; $R_f$—0.47 (Ethyl acetate:Hexane (3:7).

Step 3: Synthesis of 4-(difluoromethoxy)-8-nitrodibenzo[b,d]furan-1-carbaldehyde

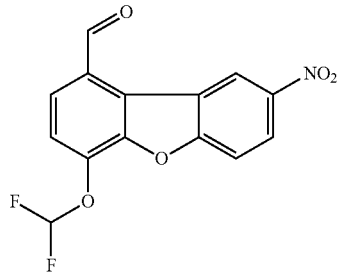 [SMILES: O=Cc1ccc(OC(F)F)c2oc3ccc([N+](=O)[O-])cc3c12]

To a mixture of 3-(2-bromo-4-nitrophenoxy)-4-(difluoromethoxy)benzaldehyde (11.5 g, 0.030 mol) and sodium acetate (3.7 g, 0.045 mol) in dimethylformamide (50 mL) palladium(II) acetate (0.68 g, 0.003 mol) was added in 4 different lots with 1 hour duration at 120-125° C. After the completion of the addition, it was refluxed for 16 hours. The reaction mixture was filtered through hyflo, washed with dimethylformamide (10 mL). The filtrate was poured into the cold water. The solid separated out was filtered. The solid was washed with hexane and dried. Yield—73.3%. HPLC (purity): 84.5%; $R_f$—0.5 (Ethyl acetate:Hexane (3:7)

Step 4: Synthesis of 4-(difluoromethoxy)-8-nitrodibenzo[b,d]furan-1-carboxylic acid

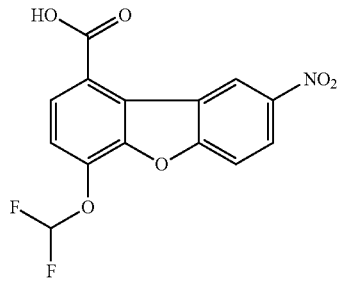 [SMILES: O=C(O)c1ccc(OC(F)F)c2oc3ccc([N+](=O)[O-])cc3c12]

To a stirring solution of 4-(difluoromethoxy)-8-nitrodibenzo[b,d]furan-1-carbaldehyde (6.5 g, 0.021 mol) and sulphamic acid (3.7 g, 0.038 mol) in acetone (25 mL) was added sodium chlorite (3.0 g, 0.033 mol) in water (25 mL) dropwise at 5-10° C. After 15 minutes, the reaction slurry was allowed to stir at room temperature for 17 hours. The reaction slurry was poured into ice-cold water and filtered. The solid obtained was washed with hexane and dried. Yield—81.9%. $^1$H-NMR (DMSO-$d_6$) δ: 7.44-7.64-7.80 (t, 2H), 8.09-8.16 (m, 2H), 8.53-8.55 (m, 1H), 9.80 (d, 1H), 13.75 (s, 1H); HPLC (purity): 87.6%; Mass calculated for $C_{14}H_7F_2NO_6$-323.2, observed—322.0; $R_f$—0.25 (Ethyl acetate:Hexane (1:1).

Step 5: Synthesis of ethyl 2-[((4-(difluoromethoxy)-8-nitrodibenzo[b,d]furan-1-yl)carbonyl)amino]-3-hydroxy propanoate

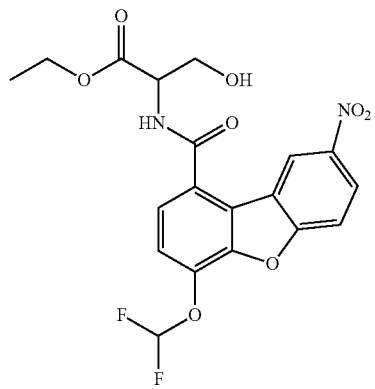 [SMILES: CCOC(=O)C(CO)NC(=O)c1ccc(OC(F)F)c2oc3ccc([N+](=O)[O-])cc3c12]

A mixture of 4-(difluoromethoxy)-8-nitrodibenzo[b,d]furan-1-Carboxylic acid (2 g, 6.19 mmol), 1-(3-dimethylaminopropyl)-3-ethylcarbodiimide.HCl (EDC) (1.31 g, 1.10 mmol), 1-hydroxybenzotriazole (HOBt) (1.0 g, 1.2 mmol) and 4-dimethylaminopyridine (0.08 g, 0.65 mmol) was dried for 30 minutes. To this dimethylformamide (10 mL) was added followed by N,N-diisopropylethyl amine (5.5 mL, 0.03 mol) at 5-10° C. After 30 minutes, ethyl 2-amino-3-hydroxy propanoate.HCl (1.85 g, 0.011 mol) was added. Then stirred at room temperature for 17 hours. The reaction mixture was poured into the cold water and filtered. The solid was washed with excess water and hexane. The product was purified by column chromatography by using dichloromethane (100%). Yield—37.2%. $^1$H-NMR (DMSO-$d_6$) δ: 1.20-1.24 (m, 3H), 3.86-3.89 (m, 2H), 4.16-4.21 (m, 2H), 4.62 (d, 1H), 5.10-5.12 (m, 1H), 7.41-7.59-7.77 (t, 1H), 7.66 (d, 1H), 7.87 (d, 1H), 8.09 (d, 1H), 8.50-8.53 (m, 1H), 9.07 (d, 1H), 9.36 (d, 1H); HPLC (purity): 96.4%; Mass calculated for $C_{19}H_{16}F_2N_2O_8$-438.3, observed—439.0; $R_f$—0.49 (Ethyl acetate:Hexane (7:3).

Step 6: Synthesis of ethyl 2-(4-(difluoromethoxy)-8-nitrodibenzo[b,d]furan-1-yl)-4,5-dihydrooxazole-4-carboxylate

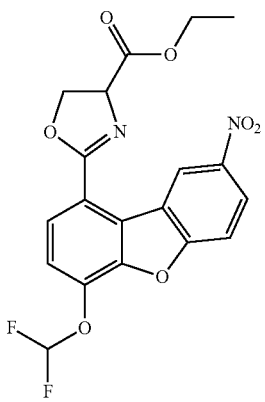 [SMILES: CCOC(=O)C1COC(c2ccc(OC(F)F)c3oc4ccc([N+](=O)[O-])cc4c23)=N1]

To a stirring solution of ethyl 2-[((4-(difluoromethoxy)-8-nitrodibenzo[b,d]furan-1-yl)carbonyl)amino]-3-hydroxy propanoate (1 g, 2.28 mmol) in dichloromethane (15 mL) was added diethylamino sulfur trifluoride (DAST) (0.8 mL, 6.53 mmol) at −78° C. After 1 hour, potassium carbonate (0.95 g, 6.87 mmol) was added. Then the reaction mass was stirred at room temperature for 30 minutes. The reaction mixture was poured into the saturated sodium bicarbonate solution (50 mL). The aqueous layer was extracted with dichloromethane (2×50 mL). The organics were dried over sodium sulphate and filtered. The solvents were removed in vacuum to give the desired product. Yield—83.4%. $^1$H-NMR (CDCl$_3$) δ: 1.38-1.41 (m, 3H), 4.40-4.45 (m, 2H), 4.70-4.75 (m, 1H), 4.81-4.86 (m, 1H), 5.18-5.23 (m, 1H), 6.69-6.87-7.06 (brs, 1H), 7.43 (d, 1H), 7.73 (d, 1H), 8.01 (d, 1H), 8.49 (d, 1H), 10.37 (s, 1H); HPLC (purity): 99.2%; Mass calculated for C$_{19}$H$_{14}$F$_2$N$_2$O$_7$-420.3, observed—421.1; R$_f$—0.49 (Ethyl acetate:Hexane (3:7).

Step 7: Synthesis of ethyl 2-(4-(difluoromethoxy)-8-nitrodibenzo[b,d]furan-1-yl)-1,3-oxazole-4-carboxylate

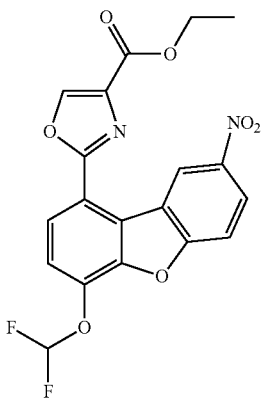 [SMILES: CCOC(=O)c1coc(-c2ccc(OC(F)F)c3oc4ccc([N+](=O)[O-])cc4c23)n1]

To a solution of ethyl 2-(4-(difluoromethoxy)-8-nitrodibenzo[b,d]furan-1-yl)-4,5-dihydrooxazole-4-carboxylate (0.8 g, 1.90 mmol) in acetonitrile (8 mL), CCl$_4$ (5 mL) and pyridine (8 mL) were added. To this mixture 1,3-diaza bicyclo [5.4.0]undec-7-ene (DBU) (1.6 mL, 10.72 mmol) was added. The reaction mass was stirred at room temperature for 1 hour. The reaction mixture was poured into the cold water (50 mL) and extracted with dichloromethane (2×50 mL). The organics were dried over sodium sulphate and filtered. The organics were evaporated under reduced pressure to give the crude product. The product was purified by column chromatography by using gradient of ethyl acetate in hexane (0-5) %. Yield—94%. $^1$H-NMR (CDCl$_3$) δ: 1.52-1.55 (m, 3H), 4.54-4.60 (m, 2H), 6.72-6.90-7.08 (brs, 1H), 7.51 (d, 1H), 7.77 (d, 1H), 8.14 (d, 1H), 8.46 (s, 1H), 8.52-8.55 (m, 1H), 10.66 (d, 1H); HPLC (purity): 97.4%; Mass calculated for C$_{19}$H$_{12}$F$_2$N$_2$O$_7$-418.3, observed—419.1; R$_f$—0.49 (Ethyl acetate:Hexane (3:7).

Example 48

Synthesis of ethyl 2-(4-(difluoromethoxy)-8-(methylsulfonamido) dibenzo[b,d]furan-1-yl)-1,3-oxazole-4-carboxylate

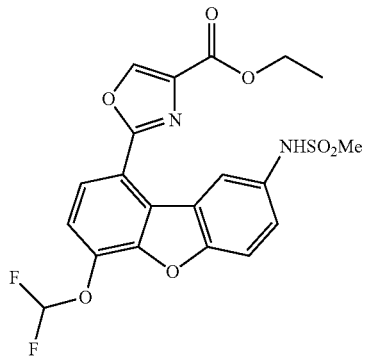

Step, 1: Synthesis of ethyl 2-(8-amino-4-(difluoromethoxy)dibenzo[b,d]furan-1-yl)1,3-oxazole-4-carboxylate

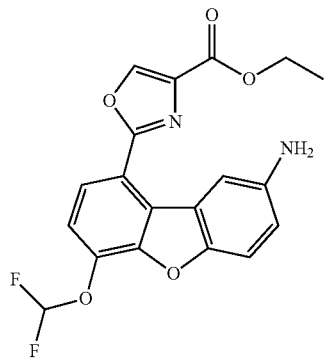 [SMILES: CCOC(=O)c1coc(-c2ccc(OC(F)F)c3oc4ccc(N)cc4c23)n1]

A mixture of methanol (100 mL) and ethyl acetate (100 mL) was added to the ethyl 2-(4-(difluoromethoxy)-8-nitrodibenzo[b,d]furan-1-yl)1,3-oxazole-4-carboxylate (0.8 g, 1.91 mmol) from step 7 of example 47. To the reaction mixture, palladium-carbon (0.30 g) was added. The reaction mixture was transferred to the hydrogenation flask and hydrogenation was performed at room temperature (40 psi-hydrogen) for 2 hours. The reaction mixture was filtered through celite. The filtrate was evaporated at reduced pressure to give the desired product. Yield—87.5%. R$_f$—0.5 (Ethyl acetate:Hexane (1:1)

Step 2: Synthesis of Ethyl 2-(4-(difluoromethoxy)-8-(methylsulfonamido) dibenzo[b,d]furan-1-yl)-1,3-oxazole-4-carboxylate

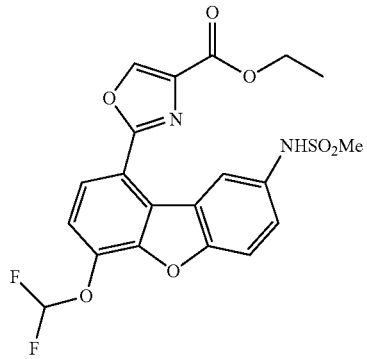

To a solution of ethyl 2-(8-amino-4-(difluoromethoxy)dibenzo[b,d]furan-1-yl)oxazole-4-carboxylate (0.65 g, 1.667 mmol) in tetrahydrofuran (10 mL) was added pyridine (0.4 mL, 5.031 mmol). To this solution was added methane sulfonyl chloride (2.6 mL, 0.033 mol) at 0-5° C. After 30 minutes, the reaction slurry was stirred at room temperature for 18 hours. The reaction mass was poured into the cold water and extracted with dichloromethane (3×50 mL). The organics were dried over sodium sulphate and filtered. The organics were evaporated under reduced pressure to give the crude product. The product was purified by column chromatography by using gradient of ethyl acetate in hexane (0-20) %. Yield—44.8%. $^1$H-NMR (DMSO-$d_6$) δ: 1.35-1.39 (m, 3H), 3.06 (s, 3H), 4.36-4.41 (m, 2H), 7.41 (s, 1H), 7.51 (d, 1H), 7.62 (d, 1H), 7.87 (d, 1H), 8.06 (d, 1H), 8.96 (s, 1H), 9.07 (s, 1H), 9.77 (s, 1H); HPLC (purity): 97.2%; Mass calculated for $C_{20}H_{16}F_2N_2O_7S$-466.4, observed—467.0; $R_f$—0.47 (Ethyl acetate:Hexane (1:1)

Example 49

Synthesis of 2-(4-(difluoromethoxy)-8-(methylsulfonamido) dibenzo[b,d]furan-1-yl)-1,3-oxazole-4-carboxylic acid

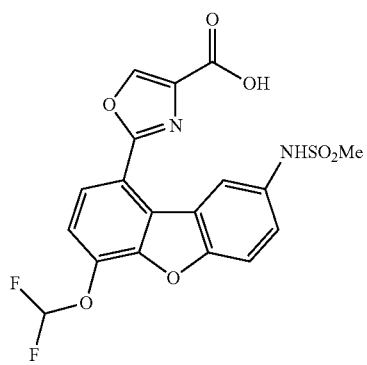

To a slurry of ethyl 2-(4-(difluoromethoxy)-8-(methylsulfonamido)dibenzo[b,d]furan-1-yl)1,3-oxazole-4-carboxylate (0.2 g, 0.429 mmol) in ethanol (5 mL) and tetrahydrofuran (3 mL) was added potassium hydroxide (0.256 g, 4.562 mmol) in water (0.5 mL). Then it was stirred at room temperature for 16 hours. The solvent was removed in vacuum. The residue was diluted with water and acidified with 1N HCl until the solid separates out. The solid was filtered and washed with hexane. Yield—98.4%. $^1$H-NMR (DMSO-$d_6$) δ: 3.09 (s, 3H), 7.40 (s, 1H), 7.48-7.51 (m, 1H), 7.59-7.63 (m, 2H), 7.87 (d, 1H), 8.06 (d, 1H), 8.97-8.99 (m, 2H), 9.81 (s, 1H); HPLC (purity): 99.1%; Mass calculated for $C_{18}K_2F_2N_2O_7S$-438.4, observed—437.0; $R_f$—0.2 (Dichloromethane:Methanol (8:2)).

Example 50

Synthesis of 2-(4-(difluoromethoxy)-8-(methylsulfoamido)dibenzo[b,d]furan-4-yl)-N-(4-hydroxycyclohexyl)-1,3-oxazole-4-carboxamide

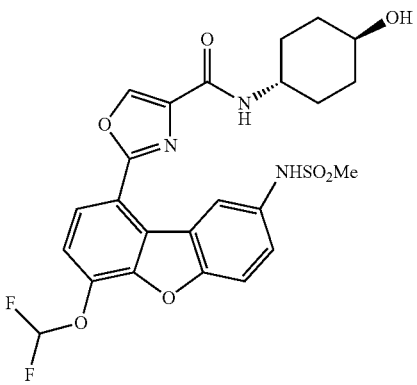

A mixture of 2-(4-(difluoromethoxy)-8-(methylsulfonamido)dibenzo[b,d]furan-1-yl)-1,3-oxazole-4-carboxylic acid (0.05 g, 0.114 mmol), 1-(3-dimethylaminopropyl)-3-ethyl carbodiimide.HCl (0.025 g, 0.130 mmol), 1-hydroxybenzotriazole (0.019 g, 0.141 mmol) and 4-dimethylaminopyridine (0.002 g, 0.016 mmol) was dried for 30 minutes. To this dimethylformamide (1 mL) was added followed by N,N-diisopropylethyl amine (0.1 mL, 0.574 mmol) at 5-10° C. After 30 minutes, trans 4-aminocyclohexanol.HCl (0.024 g, 0.158 mmol) was added and stirred at room temperature for 16 hours. The reaction mixture was poured into the cold water and filtered. The solid was washed with excess water and hexane. Yield—49.1%. $^1$H-NMR (DMSO-$d_6$) δ: 1.25-1.31 (m, 2H) 1.58-1.67 (m, 2H), 1.80-1.88 (m, 4H), 2.97 (s, 3H), 3.41-3.47 (m, 1H), 3.82-3.85 (m, 1H), 4.58 (d, 1H), 7.40-7.57-7.73 (t, 1H), 7.45-7.51 (m, 1H), 7.62 (d, 1H), 7.76 (d, 1H), 7.88 (d, 1H), 8.10 (d, 1H), 8.84 (s, 1H), 9.17 (d, 1H), 9.82 (s, 1H); HPLC (purity): 95.2%; Mass calculated for $C_{24}H_{23}F_2N_3O_7S$-535.5, observed-536.0; $R_f$—0.21 (Dichloromethane: Methanol (9.4:0.6).

The following compounds were prepared according to the procedure outlined above:

| S. No | Analytical Data | Structure |
|---|---|---|
| 51 | ¹H-NMR (DMSO-d₆) δ: 0.73 (d, 4H), 2.90 (d, 1H), 3.00 (s, 3H), 7.40-7.57-7.77 (t, 3H), 7.87 (d, 1H), 8.07-8.09 (m, 2H), 8.84 (s, 1H), 9.08 (s, 1H), 9.86 (s, 1H); Mass m/z: 478.0 (M + 1). | 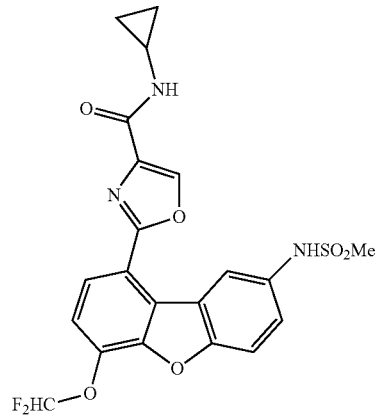 |
| 52 | ¹H-NMR (DMSO-d₆) δ: 1.56 (s, 2H) 1.66-1.68 (m, 2H), 1.76 (s, 2H), 1.93 (d, 2H), 2.98 (s, 3H), 4.32 (d, 1H), 7.40-7.59-7.77 (t, 1H), 7.49-7.51 (m, 1H), 7.63 (d, 1H), 7.87-7.91 (m, 2H), 8.09 (d, 1H), 8.83 (s, 1H), 9.13 (s, 1H), 9.83 (s, 1H); Mass m/z: 506.1 (M + 1). | 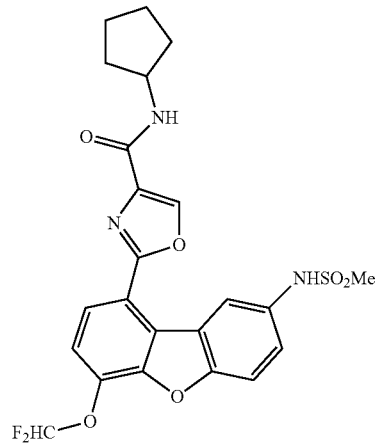 |
| 53 | ¹H-NMR (CDCl₃) δ: 1.39-1.43 (m, 3H), 2.72 (s, 3H), 4.06 (s, 3H), 4.36-4.42 (m, 2H), 7:00 (d, 1H), 7.33-7.37 (m, 1H), 7.45-7.49 (m, 1H), 7.59 (d, 1H), 7.91 (d, 1H), 9.20 (d, 1H); Mass m/z: 352.1 (M + 1). | 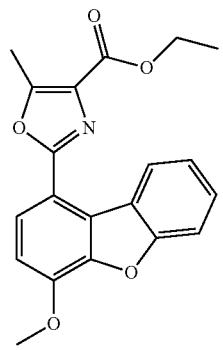 [SMILES: CCOC(=O)c1nc(-c2ccc(OC)c3oc4ccccc4c23)oc1C] |
| 54 | ¹H-NMR (DMSO-d₆) δ: 2.74 (s, 3H), 4.08 (s, 3H), 7.38 (d, 1H), 7.44-7.48 (m, 1H), 7.62-7.65 (m, 1H), 7.80 (d, 1H), 7.99 (d, 1H), 9.36 (d, 1H); Mass m/z: 324.1 (M + 1). | 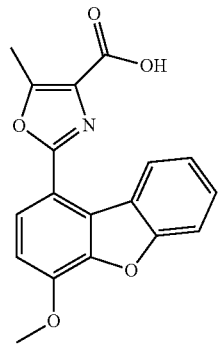 [SMILES: COc1ccc(-c2nc(C(=O)O)c(C)o2)c2c1oc1ccccc12] |

| S. No | Analytical Data | Structure |
|---|---|---|
| 55 | $^{1}$H-NMR (CDCl$_3$) δ: 2.87 (s, 3H), 4.16 (s, 3H), 7.11 (d, 1H), 7.40 (d, 1H), 7.52-7.58 (m, 1H), 7.70 (d, 1H), 7.98 (d, 1H), 8.61 (s, 2H), 8.91 (s, 1H), 9.05 (d, 1H); Mass m/z: 468.1 (M + 1). | 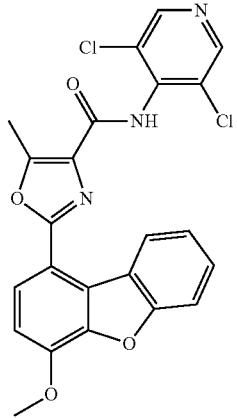 [SMILES: COc1ccc(-c2nc(C(=O)Nc3c(Cl)cncc3Cl)c(C)o2)c2c1oc1ccccc12] |
| 56 | $^{1}$H-NMR (DMSO-d$_6$) δ: 0.67-0.69 (m, 2H), 0.73-0.77 (m, 2H), 2.74 (s, 3H), 2.87-2.88 (m, 1H), 4.07 (s, 3H), 7.37 (d, 1H), 7.45-7.49 (m, 1H), 7.61-7.65 (m, 1H), 7.80 (d, 1H), 7.98 (d, 1H), 8.18 (d, 1H), 8.84 (d, 1H); Mass m/z: 363.1 (M + 1). | 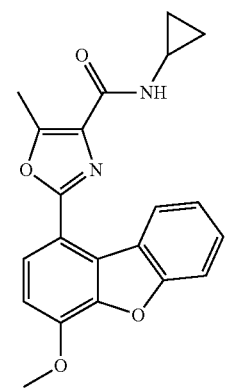 [SMILES: COc1ccc(-c2nc(C(=O)NC3CC3)c(C)o2)c2c1oc1ccccc12] |
| 57 | $^{1}$H-NMR (DMSO-d$_6$) δ: 1.14-1.18 (m, 3H), 2.75 (s, 3H), 3.31-3.37 (m, 2H), 4.08 (s, 3H), 7.38 (d, 1H), 7.45-7.49 (m, 1H), 7.61-7.65 (m, 1H), 7.80 (d, 1H), 7.98 (d, 1H), 8.18 (s, 1H), 8.91 (d, 1H); Mass m/z: 351.1 (M + 1). | 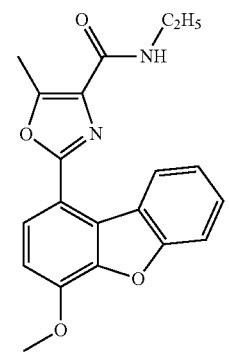 [SMILES: CCNC(=O)c1nc(-c2ccc(OC)c3oc4ccccc4c23)oc1C] |
| 58 | $^{1}$H-NMR (CDCl$_3$) δ: 2.82 (s, 3H), 4.14 (s, 3H), 5.55 (s, 1H), 6.96 (s, 1H), 7.09 (d, 1H), 7.37-7.41 (m, 1H), 7.53-7.57 (m, 1H), 7.69 (d, 1H), 7.95 (d, 1H), 8.95 (d, 1H); Mass m/z: 323.1 (M + 1). | 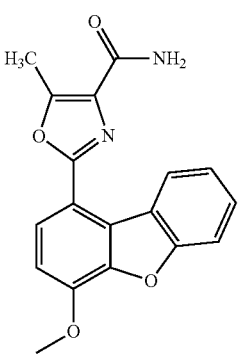 [SMILES: COc1ccc(-c2nc(C(N)=O)c(C)o2)c2c1oc1ccccc12] |

-continued

| S. No | Analytical Data | Structure |
|---|---|---|
| 59 | ¹H-NMR (CDCl₃) δ: 1.13 (d, 1H), 1.71-1.75 (m, 3H), 1.79 (d, 2H), 2.08-2.11 (m, 2H), 2.81 (s, 3H), 4.14 (s, 3H), 4.41-4.46 (m, 1H), 7.08 (d, 2H), 7.35-7.39 (m, 1H), 7.53-7.57 (m, 1H), 7.69 (d, 1H), 7.94. (d, 1H), 8.97 (d, 1H); Mass m/z: 391.1 (M + 1). | 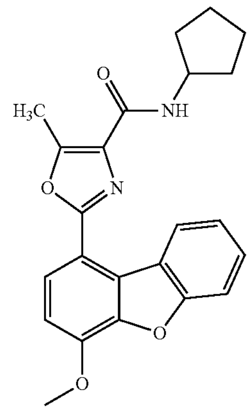 [SMILES: COc1ccc(-c2nc(C(=O)NC3CCCC3)c(C)o2)c2c1oc1ccccc12] |
| 60 | ¹H-NMR (CDCl₃) δ: 1.36-1.53 (m, 5H), 2.07 (d, 2H), 2.17 (d, 2H), 2.82 (s, 3H), 3.71 (s, 1H), 3.98-4.00 (m, 1H), 4.14 (s, 3H), 6.97 (d, 1H), 7.08 (d, 1H), 7.35-7.39 (m, 1H), 7.53-7.57 (m, 1H), 7.69 (d, 1H), 7.93 (d, 1H), 8.90 (d, 1H); Mass m/z: 421.1 (M + 1). | 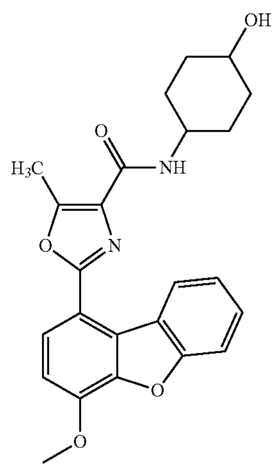 [SMILES: COc1ccc(-c2nc(C(=O)NC3CCC(O)CC3)c(C)o2)c2c1oc1ccccc12] |
| 61 | ¹H-NMR (CDCl₃) δ: 1.29-1.33 (m, 6H), 2.82 (s, 3H), 4.14 (s, 3H), 4.27-4.33 (m, 1H), 6.96 (d, 1H), 7.08 (d, 1H), 7.36-7.40 (m, 1H), 7.53-7.57 (m, 1H), 7.69 (d, 1H), 7.94 (d, 1H), 8.93 (d, 1H); Mass m/z: 365.1 (M + 1). | 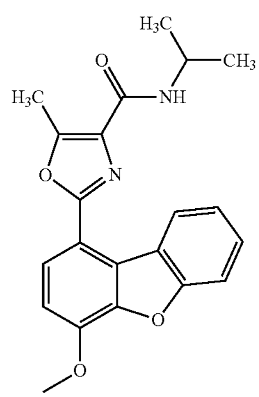 [SMILES: COc1ccc(-c2nc(C(=O)NC(C)C)c(C)o2)c2c1oc1ccccc12] |
| 62 | ¹H-NMR (CDCl₃) δ: 1.45-1.48 (m, 3H), 4.14 (s, 3H), 4.45-4.50 (m, 2H), 7.09 (d, 1H), 7.43-7.45 (m, 1H), 7.55 (d, 1H), 7.67 (d, 1H), 8.04 (d, 1H), 8.39 (s, 1H), 9.23 (d, 1H); Mass m/z: 338.1 (M + 1). | 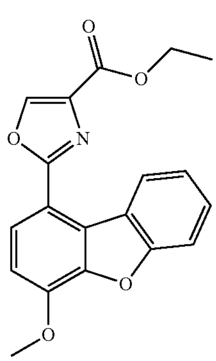 [SMILES: CCOC(=O)c1coc(-c2ccc(OC)c3oc4ccccc4c23)n1] |

| S. No | Analytical Data | Structure |
|---|---|---|
| 63 | ¹H-NMR (DMSO-d$_6$) δ: 4.09 (s, 3H), 7.40 (d, 1H), 7.44-7.48 (m, 1H), 7.62-7.65 (m, 1H), 7.80 (d, 1H), 8.03 (d, 1H), 8.95 (s, 1H), 9.36 (d, 1H), 13.27 (s, 1H); Mass m/z: 310.1 (M + 1). | 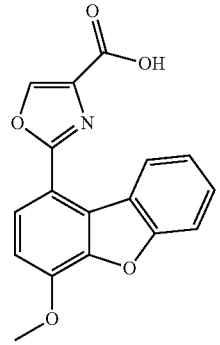 [SMILES: COc1ccc(-c2nc(C(=O)O)co2)c2c1oc1ccccc12] |
| 64 | ¹H-NMR (CDCl$_3$) δ: 1.36-1.40 (m, 3H), 3.93 (s, 2H), 4.14 (d, 4H), 4.15 (s, 3H), 4.33-4.38 (m, 4H), 7.11 (d, 1H), 7.39-7.43 (m, 1H), 7.55-7.58 (m, 1H), 7.70 (d, 1H), 8.03 (d, 1H), 8.38 (s, 1H), 8.88 (s, 2H), 9.12 (d, 1H); Mass m/z: 528.2 (M + 1). | 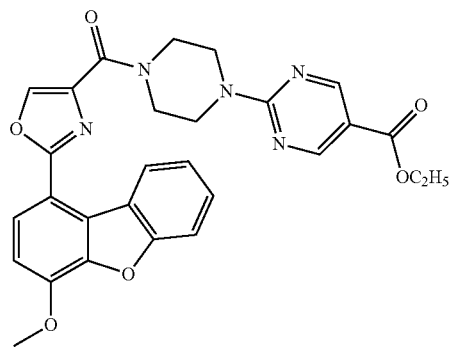 [SMILES: CCOC(=O)c1cnc(N2CCN(C(=O)c3coc(-c4ccc(OC)c5oc6ccccc6c45)n3)CC2)nc1] |
| 65 | ¹H-NMR (CDCl$_3$) δ: 4.17 (s, 3H), 7.13 (d, 1H), 7.38-7.42 (m, 1H); 7.55-7.59 (m, 1H), 7.71 (d, 1H), 8.04 (d, 1H), 8.53 (s, 1H), 8.62 (s, 2H), 8.88 (s, 1H), 9.02 (d, 1H); Mass m/z: 454.1 (M + 1). | 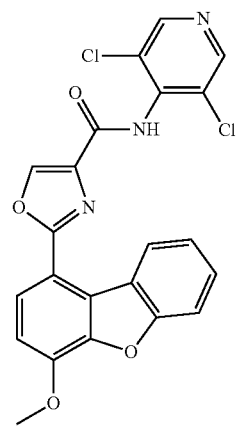 [SMILES: COc1ccc(-c2nc(C(=O)Nc3c(Cl)cncc3Cl)co2)c2c1oc1ccccc12] |
| 66 | ¹H-NMR (DMSO-d$_6$) δ: 3.78-3.84 (m, 2H), 4.03 (d, 4H), 4.09 (s, 3H), 4.11-4.15 (m, 2H), 7.41 (d, 1H), 7.49 (s, 1H), 7.67 (s, 1H), 7.82 (d, 1H), 8.08 (d, 1H), 8.73 (s, 1H), 8.81 (s, 2H), 9.18 (d, 1H); Mass m/z: 500.4 (M + 1). | 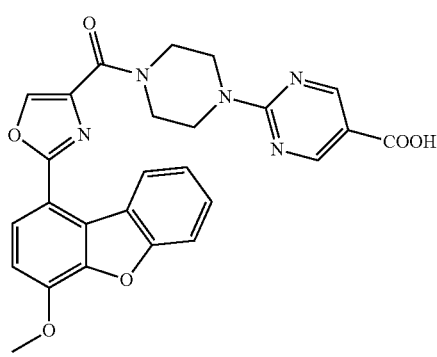 [SMILES: COc1ccc(-c2nc(C(=O)N3CCN(c4ncc(C(=O)O)cn4)CC3)co2)c2c1oc1ccccc12] |

| S. No | Analytical Data | Structure |
|---|---|---|
| 67 | ¹H-NMR (CDCl₃) δ: 4.15 (s, 3H), 5.80 (s, 1H), 6.97 (s, 1H), 7.10 (d, 1H), 7.38-7.42 (m, 1H), 7.54-7.58 (m, 1H), 7.69 (d, 1H), 7.99 (d, 1H), 8.41 (s, 1H), 8.92 (s, 1H); Mass m/z: 309.1 (M + 1). | 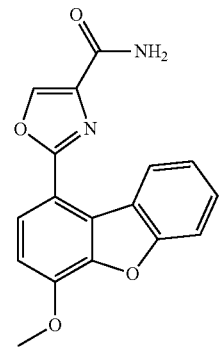 [SMILES: COc1ccc(-c2nc(C(N)=O)co2)c2c1oc1ccccc12] |
| 68 | ¹H-NMR (CDCl₃) δ: 3.92 (s, 2H), 4.01-4.03 (m, 4H), 4.15 (s, 3H), 4.37 (s, 2H), 6.55-6.57 (m, 1H), 7.11 (d, 1H), 7.40-7.43 (m, 1H), 7.52-7.58 (m, 1H), 7.69 (d, 1H), 8.03 (d, 1H), 8.35-8.37 (m, 3H), 9.15 (d, 1H); Mass m/z: 456.2 (M + 1). | 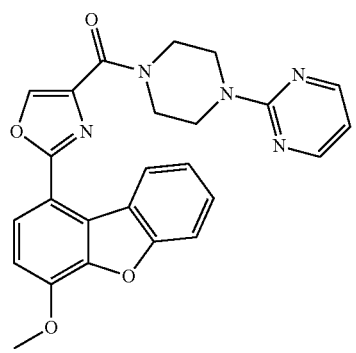 [SMILES: COc1ccc(-c2nc(C(=O)N3CCN(c4ncccn4)CC3)co2)c2c1oc1ccccc12] |
| 69 | ¹H-NMR (CDCl₃) δ: 3.08 (d, 3H), 4.15 (s, 3H), 7.06 (s, 1H), 7.10 (d, 1H), 7.40-7.43 (m, 1H), 7.52-7.58 (m, 1H), 7.69 (d, 1H), 7.98 (d, 1H), 8.37 (s, 1H), 8.86 (d, 1H); Mass m/z: 323.1 (M + 1). | 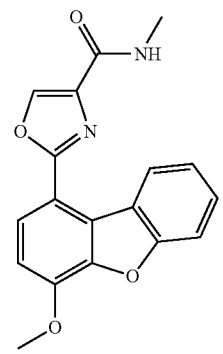 [SMILES: CNC(=O)c1coc(-c2ccc(OC)c3oc4ccccc4c23)n1] |
| 70 | 1H-NMR (CDCl₃) δ: 0.70-0.73 (m, 2H), 0.91-0.95 (m, 2H), 2.94-2.99 (m, 1H), 4.15 (s, 3H), 7.10 (d, 1H), 7.13 (s, 1H), 7.38-7.42 (m, 1H), 7.52-7.58 (m, 1H), 7.69 (d, 1H), 7.97 (d, 1H), 8.37 (s, 1H), 8.83 (d, 1H); Mass m/z: 349.1 (M + 1). | 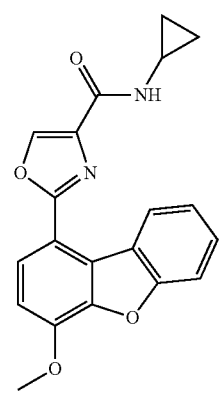 [SMILES: COc1ccc(-c2nc(C(=O)NC3CC3)co2)c2c1oc1ccccc12] |

| S. No | Analytical Data | Structure |
|---|---|---|
| 71 | $^1$H-NMR (CDCl$_3$) δ: 1.95-2.04 (m, 4H), 3.71-3.75 (m, 4H), 4.13-4.16 (m, 3H), 7.10 (d, 1H), 7.36-7.40 (m, 1H), 7.52-7.57 (m, 1H), 7.68 (d, 1H), 8.01 (d, 1H), 8.38 (d, 1H), 9.11 (d, 1H); Mass m/z: 363.1 (M + 1). | 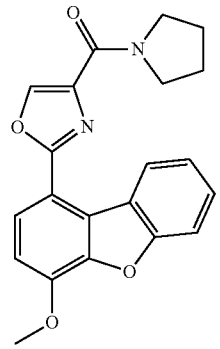 [SMILES: COc1ccc(-c2nc(C(=O)N3CCCC3)co2)c2c1oc1ccccc12] |
| 72 | $^1$H-NMR (DMSO-d$_6$) δ: 4.13 (s, 3H), 7.46 (d, 1H), 7.52-7.56 (m, 1H), 7.65-7.69 (m, 1H), 7.84 (d, 1H), 7.97 (d, 1H), 8.10 (d, 1H), 8.28 (d, 1H), 8.47 (s, 1H), 9.47 (d, 1H), 13.17 (s, 1H); Mass m/z: 360.0 (M + 1). | 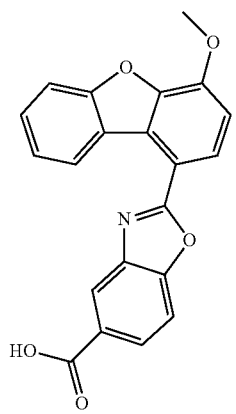 [SMILES: COc1ccc(-c2nc3cc(C(=O)O)ccc3o2)c2c1oc1ccccc12] |
| 73 | $^1$H-NMR (DMSO-d$_6$) δ: 4.12 (s, 3H), 7.44-7.54 (m, 3H), 7.66 (s, 1H), 7.84 (d, 1H), 7.92 (d, 1H), 8.02 (d, 1H), 8.17 (s, 1H), 8.26 (d, 1H), 8.49 (s, 1H), 9.47 (d, 1H); Mass m/z: 359.1 (M + 1). | 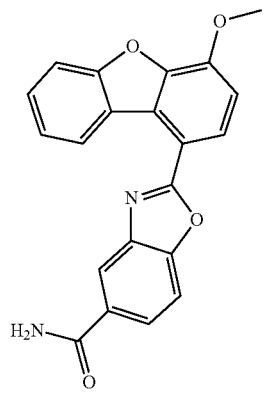 [SMILES: COc1ccc(-c2nc3cc(C(N)=O)ccc3o2)c2c1oc1ccccc12] |
| 74 | $^1$H-NMR (CDCl$_3$) δ: 4.17 (s, 3H), 7.14 (d, 1H), 7.40-7.42 (m, 2H), 7.46-7.48 (m, 1H), 7.55-7.57 (m, 1H), 7.65-7.70 (m, 2H), 7.88-7.91 (m, 1H), 8.23 (d, 1H), 9.39 (d, 1H); Mass m/z: 316.1 (M + 1). | 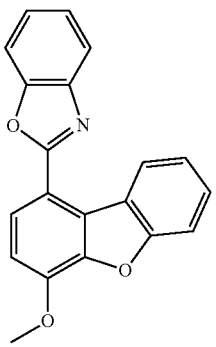 [SMILES: COc1ccc(-c2nc3ccccc3o2)c2c1oc1ccccc12] |

-continued

| S. No | Analytical Data | Structure |
|---|---|---|
| 75 | $^1$H-NMR (CDCl$_3$) δ: 4.18 (s, 3H), 7.15 (d, 1H), 7.33-7.36 (m, 1H), 7.47-7.51 (m, 1H), 7.57-7.60 (m, 1H), 7.69 (d, 1H), 7.93 (d, 1H), 8.31 (d, 1H), 8.64 (s, 1H), 9.66 (d, 1H); Mass m/z: 317.1 (M + 1). | 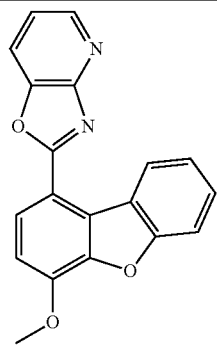 |
| 76 | $^1$H-NMR (DMSO-d$_6$) δ: 1.57 (s, 2H) 1.71-1.79 (m, 4H), 2.14-2.17 (m, 2H), 4.17 (s, 3H), 4.45-4.51 (m, 1H), 6.15 (d, 1H), 7.15 (d, 1H), 7.47-7.49 (m, 1H), 7.57-7.60 (m, 1H), 7.67-7.71 (m, 2H), 7.90 (d, 1H), 8.24 (d, 2H), 9.45 (d, 1H); Mass m/z: 427.1 (M + 1). | 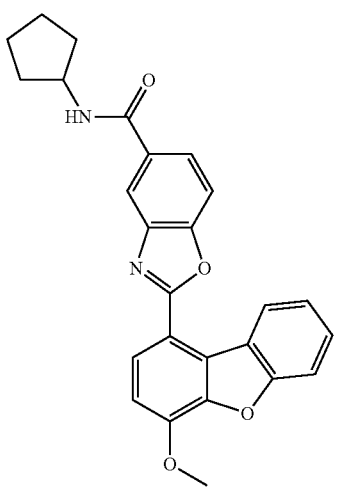 [SMILES: COc1ccc(-c2nc3cc(C(=O)NC4CCCC4)ccc3o2)c2c1oc1ccccc12] |
| 77 | $^1$H-NMR (DMSO-d$_6$) δ: 1.24-1.32 (m, 2H) 1.39-1.48 (m, 2H), 1.88 (d, 4H), 3.38-3.43 (m, 1H), 3.78-3.80 (m, 1H), 4.12 (s, 3H), 4.59 (d, 1H), 7.46 (d, 1H), 7.51-7.55 (m, 1H), 7.65-7.69 (m, 1H), 7.84 (d, 1H), 7.91 (d, 1H), 7.99-8.01 (m, 1H), 8.27 (d, 1H), 8.38 (d, 1H), 8.47 (s, 1H), 9.52 (d, 1H); Mass m/z: 457.1 (M + 1). | 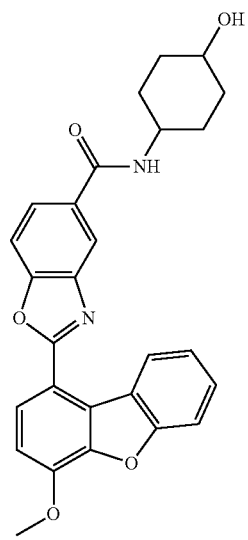 [SMILES: COc1ccc(-c2nc3cc(C(=O)NC4CCC(O)CC4)ccc3o2)c2c1oc1ccccc12] |

Biological Activity

In Vitro Measurement of Tumor Necrosis Factor Alpha (TNF-α):

This assay determines the effect of test compounds on the production of TNF-α in human Peripheral Blood Mononuclear Cells (PBMC). Compounds were tested for their ability to inhibit the activity of TNF α in human PBMC. PBMC were isolated from blood (of healthy volunteers) using BD Vacutainer CPT™ (Cell preparation tube, BD Bio Science) and suspended in RPMI (Rosewell park memorial institute) medium (*Physiol. Res.* 2003, 52, 593-598). The test compounds were pre-incubated with PBMC (0.5 million/incubation well) for 15 minutes at 37° C. and then stimulated with Lipopolysaccharide (*Escherichia coli*: B4; 1 μg/mL) for 18 h at 37° C. in 5% CO$_2$. The levels of TNF-α in the cell culture medium were estimated using enzyme-linked immunosorbent assay performed in a 96 well format as per the procedure of the manufacturer (Cayman Chemical, Ann Arbor, USA). Representative results of TNF-α inhibition are shown in the Table I.

TABLE I

TNF-α inhibition

| Ex. No | Human PBMC % inhibition of TNF-α 100 nM |
|---|---|
| 2 | 26.1 |
| 13 | 26.1 |
| 14 | 14.5 |
| 25 | 35.5 |
| 26 | 21.9 |
| 27 | 82.7 |
| 28 | 0.88 |
| 29 | 18.4 |
| 30 | 21.9 |
| 31 | 63.15 |
| 32 | NA |
| 33 | NA |
| 34 | 25.13 |
| 35 | 61.8 |
| 36 | 15.5 |
| 37 | 35.4 |
| 38 | 83.4 |
| 39 | 77.7 |
| 40 | 26.7 |
| 41 | 23.5 |
| 42 | 8.5 |
| 43 | NA |
| 44 | 17.2 |
| 45 | NA |
| 46 | 78.57 |

NA: Not active

Phosphodiesterase 4 Screening Assay:

PDE4 (Phosphodiesterase type IV) enzymes convert cyclic AMP (cAMP) into AMP. The assay is performed to determine the effect of test compounds on the inhibition of purified human PDE4B enzyme.

The assay involves the detection of the Tritiated AMP (product) using SPA beads known as yittrium silicate. The linear AMP bind preferentially to SPA yittrium silicate beads compared to cyclic nucleotides in the presence of zinc sulphate. The binding of the radiolabelled product to the bead brings the isotope into close proximity to allow radiation from the tritium to excite the scintillant within the bead to emit light. The unbound radiolabel is not close enough to allow this energy transfer and the light emitted due to the binding of tritiated AMP is detected as cpm (counts per minute).

PDE Activity (SPA Based Assay Protocol):

PDE4B activity was inhibited by the compounds according to the invention in a modified SPA (scintillation proximity assay) test, supplied by GE Healthcare Life Sciences (see procedural instructions "Phosphodiesterase [$^3$H]-cAMP SPA enzyme assay, code TRKQ 7090"), carried out in 96-well microtitre plates. The test volume is 100 μL and contains 50 mM Tris buffer (pH 7.4), 8.3 mM $Mg^{2+}$, in the presence of inhibitor or test compound, and containing PDE4B2 enzyme (sufficient to ensure that 10-20% of the cAMP is converted, under the said experimental conditions). The final concentration of DMSO in the assays (1% v/v) does not substantially affect the activity of the PDEs investigated. After a pre-incubation of 5 minutes at 37° C., the reaction is started by adding the substrate (cAMP; 0.5 μM cAMP, including about 50,000 cpm of [$^3$H]-cAMP) and the assays are incubated for a further 10 minutes; after that, they are stopped by adding SPA beads containing 18 mM $ZnSO_4$ (50 μl). After the beads have been sedimented (>30 minutes), the microtitre plates are analyzed in a Microplate luminescence detection device (TopCount* NXT; PerkinElmer Life Sciences). Where, the signal in the absence of enzyme is defined as the background. 100% activity was defined as the signal detected in the presence of enzyme and DMSO with the background subtracted. The corresponding $IC_{50}$ values of the compounds for the inhibition of PDE4B2 activity are determined from the concentration-effect curves by means of non-linear regression fit of the standard 4-parameter/multiple binding sites equation from a eight- to ten-point titration. Representative results of PDE4B inhibition are shown in the Table II at 100 nM. (Catherine B. et al. *Anal. Biochem.*, 1999, 275(2), pp. 148-155, David M. E. *Biochem. Pharmacol.*, 1999, 57, pp. 965-973)

TABLE II

% of PDE4B inhibtion at 100 nM

| Ex. No | % Inhibition PDE4B Inhibition 100 nM |
|---|---|
| 8 | 5.16 |
| 11 | 32.76 |
| 12 | 8.92 |
| 13 | 70.34 |
| 14 | 42.27 |
| 15 | 17.55 |
| 16 | 36.01 |
| 17 | 2.42 |
| 18 | 25.79 |
| 19 | 21.91 |
| 20 | 2.98 |
| 21 | 9.10 |
| 22 | 19.41 |
| 23 | 16.79 |
| 25 | 15.44 |
| 49 | 59.49 |
| 57 | 32.53 |
| 58 | 64.09 |
| 59 | NA |
| 60 | 47.28 |
| 61 | 44.29 |
| 66 | 18.92 |
| 67 | 22.79 |
| 69 | 33.26 |
| 70 | 2.34 |
| 71 | 20.34 |
| 72 | 22.23 |
| 73 | 18.08 |
| 74 | 54.86 |
| 75 | 37.22 |
| 76 | 48.31 |
| 77 | 55.28 |

LPS Induced Sepsis for Measurement of TNF-α Inhibition in Mice:

The LPS induced sepsis model in mice was performed as described by Les sekut et al (J Lab Clin Med 1994; 124, 813-20). Female Swiss albino mice were selected and the body weights were equivalent within each group. The mice were fasted for 20 h with free access to water. The mice were dosed orally with the test compound suspended in vehicle containing 0.5% Tween 80 in 0.25% Carboxy-methylcellulose sodium salt. The control mice were administered the vehicle alone. After 30 minutes of oral dosing, mice were injected with 500 μg of Lipopolysaccharide (*Escherichia coli*, LPS: B4 from Sigma) in phosphate buffer saline solution into the intraperitoneal cavity of the mice. After 90 minutes of LPS administration mice were bled via retro-orbital sinus puncture. Blood samples were stored overnight at 4° C. Serum samples were collected by centrifuging the samples at 4000 rpm for 15 minutes at 4° C. Immediately the serum samples were analysed for TNF-α levels using commercially available mouse TNF-α ELISA kit (Amersham Biosciences)

and assay was performed by the manufacturer instruction. Representative results of TNF-α inhibition are shown in the Table III.

TABLE III

TNF-α inhibition

| Ex. No | TNF-α Inhibition (%) at 10 mg/kg |
|---|---|
| 11 | 46.70 |
| 13 | 37.83 |
| 14 | 40.67 |
| 50 | 13.15 |

LPS Induced Neutrophilia Model for Asthma and COPD:

LPS induced neutrophilia in Sprague Dawley rats was performed using the protocol described in Pulm *Pharmacol & Ther* 17,133-140, 2004. Male Sprague. Dawley rats were acclimatized to laboratory conditions five to seven days prior to the start of the experiment. They were randomly distributed to various groups based on body weight. Except normal group all the animals were exposed to LPS 100 μg/ml for 40 minutes. The rats were dosed with the test compound suspended in the vehicle containing 0.25% carboxymethylcellulose before half an hour of LPS exposure. BAL was performed 6 h after LPS exposure, total cell count and DLC was done and compared with control and the standard drug. Percentage Inhibition for neutrophilia was calculated and is shown in Table IV.

TABLE IV

Inhibition of neutrophilia

| Ex. No | Dose (mg/kg) | LPS induced neutrophilia % inhibition |
|---|---|---|
| 35 | 10 | 19.29 |
| 38 | 5 | 35.68 |
| 39 | 10 | 57.98 |

We claim:
1. Compound of formula (I),

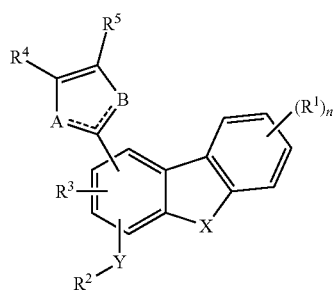

(I)

their tautomeric forms, regioisomers, stereoisomers, solvates and pharmaceutically acceptable salts thereof;
wherein:
X represents O, S;
Y represents O;
$R^3$, $R^4$ and $R^5$ independently represent hydrogen, halogens, haloalkyl, nitro, cyano, hydroxy, substituted or unsubstituted groups selected from alkyl, alkylthio, alkoxy, aryl, aryloxy, aralkyl, alkenyl, alkynyl, aralkenyl, aralkynyl, cycloalkyl, cycloalkenyl, cycloalkynyl, heterocyclyl, heteroaryl, heteroarylalkyl, —$(CH_2)_m$—C(O)N$R^7R^8$, amino, imino, alkylamino, cycloalkylamino, arylamino, aralkylamino, alkanoyl, aroyl, aralkanoyl, sulfonyl, alkylsulfonyl, arylsulfonyl, aminosulfonyl, alkylsulfonamido, —COO$R^7$, —C(O)$R^7$, —C(S)$R^7$, —C(O)N$R^7R^8$, —N$R^7$C(O)N$R^7R^8$, —N($R^7$)SO$R^8$, —N($R^7$)SO$_2R^8$, —N$R^7$C(O)O$R^8$, —N$R^7R^8$, —N$R^7$C(O)$R^8$, —N$R^7$C(S)$R^8$, —SON$R^7R^8$, —SO$_2$N$R^7R^8$; —O$R^7$, —O$R^7$C(O)O$R^8$, —CON$R^7$O$R^8$, —OC(O)$R^7$, —OC(O)N$R^7R^8$, —$R^7$N$R^7R^8$, —$R^7$O$R^8$, —S$R^7$, —SO$R^7$ and —SO$_2R^7$; $R^7$ and $R^8$ each independently represents hydrogen, substituted or unsubstituted groups selected from alkyl, aryl, aralkyl, cycloalkyl, heterocyclyl, heteroaryl and heteroarylalkyl or $R^7$ and $R^8$ can be combined together to form an substituted or unsubstituted 3-7 membered ring having 0-2 hetero atoms;
$R^1$ represents hydrogen, halogens, haloalkyl, nitro, cyano, hydroxy, substituted or unsubstituted groups selected from alkyl, alkylthio, alkoxy, aryl, aryloxy, aralkyl, alkenyl, alkynyl, aralkenyl, aralkynyl, cycloalkyl, cycloalkenyl, cycloalkynyl, heterocyclyl, heteroarylalkyl, —$(CH_2)_m$—C(O)N$R^7R^8$, amino, imino, alkylamino, cycloalkylamino, arylamino, aralkylamino, alkanoyl, aroyl, aralkanoyl, sulfonyl, alkylsulfonyl, arylsulfonyl, aminosulfonyl, alkylsulfonamido, —COO$R^7$, —C(O)$R^7$, —C(S)$R^7$, —C(O)N$R^7R^8$, —N$R^7$C(O)N$R^7R^8$, —N($R^7$)SO$R^8$, —N($R^7$)SO$_2R^8$, —N$R^7$C(O)O$R^8$, —N$R^7R^8$, —N$R^7$C(O)$R^8$, —N$R^7$C(S)$R^8$, —SON$R^7R^8$, —SO$_2$N$R^7R^8$; —O$R^7$, —O$R^7$C(O)O$R^8$, —CON$R^7$O$R^8$, —OC(O)$R^7$, —OC(O)N$R^7R^8$, —$R^7$N$R^7R^8$, —$R^7$O$R^8$, —S$R^7$, —SO$R^7$ and —SO$_2R^7$; $R^7$ and $R^8$ each independently represents hydrogen, substituted or unsubstituted groups selected from alkyl, aryl, aralkyl, cycloalkyl, heterocyclyl, heteroaryl and heteroarylalkyl or $R^7$ and $R^8$ can be combined together to form an substituted or unsubstituted 3-7 membered ring having 0-2 hetero atoms;
$R^2$ represents substituted or unsubstituted groups selected from alkyl, haloalkyl and cycloalkyl;
$R^4$ and $R^5$ can be combined together to form a substituted or unsubstituted 5 to 7 membered ring, having 0-3 heteroatoms selected from 0, N and S;
'===' represents a double bond or a single bond;
A or B represents —C$R^6$—, —N$R^6$—, =N—, —O— or —S—; when one of A or B represents —C$R^6$—, then the other represents —N$R^6$—, =N—, —O— or —S—;
$R^6$ represents hydrogen, substituted or unsubstituted groups selected from alkyl, cycloalkyl, cycloalkenyl, cycloalkynyl, aryl, aralkyl, alkenyl, alkynyl, aralkenyl, aralkynyl, heterocyclyl and heteroaryl; and
m and n are integers independently selected from 0, 1, 2, 3 or 4;
wherein the term "substituted" refers to substitution with any one or any combination of the following substituents: halogens; hydroxy; nitro; cyano; oxo (=O); thioxo (=S); azido; nitroso; amino; hydrazino; formyl; alkyl; haloalkyl groups; haloalkoxy; arylalkoxy groups; cycloalkyl; —O-cycloalkyl; aryl; alkoxy; heterocyclyl; heteroaryl; alkylamino; —O—$CH_2$-cycloalkyl; —COO$R^a$; —C(O)$R^b$; —C(S)$R^a$; —C(O)N$R^aR^b$; —N$R^a$C(O)N$R^bR^c$; —N($R^a$)SO$R^b$; —N($R^a$)SO$_2R^b$; —N$R^a$C(O)O$R^b$; —N$R^aR^b$; —N$R^a$C(O)$R^b$; —N$R^a$C(S)$R^b$; —SON$R^aR^b$; —SO$_2$N$R^aR^b$; —O$R^a$; —O$R^a$C(O)O$R^b$; —OC(O)N$R^aR^b$; —OC(O)$R^a$; —$R^a$N$R^bR^c$; —$R^a$O$R^b$; —ST$^a$; —SO$R^a$ and —SO$_2R^a$; $R^a$, $R^b$ and $R^c$ each independently represents hydrogen atom; substituted or unsubstituted groups selected from alkyl; alkylene; aryl; aralkyl; cycloalkyl; heterocyclyl; heteroaryl and heteroarylalkyl; $R^a$, $R^b$ and $R^c$ can be combined together to form a 3-7 membered ring having 0-2 hetero atoms; the substituents are further optionally substituted by one or more substituents as defined above.

2. The compound according to claim 1, wherein: when alkyl group is present, the alkyl group is methyl, ethyl, n-propyl, isopropyl, butyl, isobutyl, t-butyl, pentyl, hexyl, heptyl or octyl; when alkenyl group is present, the alkenyl group is ethenyl, 1-propenyl, 2-propenyl, iso-propenyl, 2-methyl-1-propenyl, 1-butenyl or 2-butenyl; when the alkynyl group is present, the alkynyl group is ethynyl, propynyl or butynyl; when haloalkyl group is present, the haloalkyl group is difluoromethyl, dichloromethyl, trifluoromethyl, tribromomethyl or trichloromethyl; when haloalkoxy group is present, the haloalkoxy group is selected from chloromethoxy, chloroethoxy, difluoromethoxy, dichloromethoxy, trifluoromethoxy, trifluoroethoxy and trichloromethoxy; when aryl group is present, the aryl group is phenyl, naphthyl, anthracenyl, indanyl or biphenyl; when alkoxy group is present, the alkoxy group is selected from methoxy, ethoxy, n-propoxy, isopropoxy, n-butoxy, isobutoxy or t-butoxy; when aryloxy group is present, the aryloxy group is selected from phenoxy or naphthyloxy; when aralkyl group is present, the aralkyl group is —$CH_2C_6H_5$ or —$C_2H_4C_6H_5$; when aralkenyl group is present, the aralkenyl group is phenylethenyl or phenylpropenyl; when aralkynyl group is present, the aralkynyl group is phenylethynyl or phenylpropynyl; when alkanoyl group is present, the alkanoyl group is acetyl, propanoyl or butanoyl; when aroyl group is present, the aroyl group is benzoyl or naphthoyl; when aralkanoyl group is present, the aralkanoyl group is phenylacetyl, phenylpropanoyl, naphthylacetyl or naphthylpropanoyl; when heterocyclyl or heteroaryl group is present, the heterocyclyl or heteroaryl group is selected from azetidinyl, acridinyl, benzodioxolyl, benzodioxanyl, benzofuranyl, carbazolyl, cinnolinyl, dioxolanyl, dibenzofuranyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazolyl, imidazolyl, tetrahydroisoquinolinyl, 2-oxoazepinyl, azepinyl, pyrrolyl, piperonyl, pyrrolidinyl, pyrazinyl, pyrimidinyl, pyridazinyl, pyrazolyl, oxazolyl, oxazolinyl, triazolyl, isoxazolyl, isoxazolidinyl, thiazolyl, thiazolinyl, thiazolidinyl, thienyl, isothiazolyl, quinuclidinyl, isothiazolidinyl, indolyl, isoindolyl, indolinyl, isoindolinyl, octahydroindolyl, octahydroisoindolyl, decahydroisoquinolyl, benzimidazolyl, thiadiazolyl, benzopyranyl, benzothiazolyl, benzothiadiazolyl, benzoxadiazolyl, benzotriazolyl, benzothienyl, benzoxazolyl, oxadiazolyl, benzindazolyl, indazolyl, phenyl piperidinyl, furyl, tetrahydrofuryl, tetrahydropyranyl, piperazinyl, homopiperazinyl, piperidyl, piperidopiperidyl, morpholinyl, thiomorpholinyl, piperidonyl, 2-oxopiperazinyl, 2-oxopiperidinyl, 2-oxopyrrolidinyl, oxazolidinyl, chromanyl and isochromanyl; when cycloalkyl group is present, the cycloalkyl group is cyclopropyl, cyclobutyl, cyclopentyl, cyclohexyl, cyclooctyl, cycloheptyl, perhydronaphthyl, adamantyl, bridged cyclic groups or spirobicyclic groups; when cycloalkenyl group is present, the cycloalkenyl group is cyclopropenyl or cyclopentenyl; when cycloalkynyl group is present, the cycloalkynyl group is cyclopropynyl or cyclopentynyl; when alkylsulfonyl group is present, the alkylsulfonyl group is methylsulfonyl, ethylsulfonyl, n-propylsulfonyl or isopropylsulfonyl; when arylsulfonyl group is present the arylsulfonyl group is phenylsulfonyl or naphthylsulfonyl; when alkylthio group is present, the alkylthio group is —$SCH_3$ or —$SC_2H_5$; when alkylamino group is present, the alkylamino group is —$NHCH_3$ or —$N(CH_3)_2$ and when arylamino group is present, the arylamino group is phenylamino or naphthylamino.

3. A compound of formula (I) as defined in claim 1 selected from the compounds consisting of:

Ethyl 6-(2-(4-methoxydibenzo[b,d]furan-1-yl)-1,3-thiazol-4-yl)picolinate;

6-(2-(4-Methoxydibenzo[b,d]furan-1-yl)-1,3-thiazol-4-yl)picolinic acid;

Ethyl 6-(2-(4-ethoxydibenzo[b,d]furan-1-yl)-1,3-thiazol-4-yl)picolinate;

6-(2-(4-Ethoxydibenzo[b,d]furan-1-yl)-1,3-thiazol-4-yl)picolinic acid;

Ethyl 6-(2-(4-(difluoromethoxy)dibenzo[b,d]furan-1-yl)-1,3-thiazol-4-yl)picolinate;

6-(2-(4-(Difluoromethoxy)dibenzo[h,d]furan-1-yl)-1,3-thiazol-4-yl)picolinic acid;

4-(2-(4-Methoxydibenzo[M]furan-1-yl)-1,3-thiazol-4-yl)benzonitrile;

6-(2-(4-Methoxydibenzo[b,d]furan-2-yl)-1,3-thiazol-4-yl)picolinic acid;

6-(2-(4-Methoxy-8-(methylsulfonamido)dibenzo[b,d]furan-2-yl)-1,3-thiazol-4-yl)picolinic acid;

N-(3,5-Dichloropyridin-4-yl)-3-(2-(4-methoxydibenzo[b,d]furan-1-yl)-1,3-thiazol-4-yl)propanamide;

N-(3,5-Dichloropyridin-4-yl)-2-(2-(4-methoxydibenzo[b,d]furan-1-yl)-1,3-thiazol-4-yl)acetamide;

N-(3,5-Dichloropyridin-4-yl)-2-(4-methoxydibenzo[b,d]furan-1-yl)-1,3-thiazole-4-carboxamide;

N-(3,5-Dichloropyridin-4-yl)-2-(4-(difluoromethoxy)dibenzo[b,d]furan-1-yl)-1,3-thiazole-4-carboxamide;

Ethyl 2-(4-methoxydibenzo[b,d]furan-1-yl)-1,3-thiazole-4-carboxylate;

2-(4-Methoxydibenzo[b,d]furan-1-yl)-1,3-thiazole-4-carboxylic acid;

2-(4-Methoxydibenzo[b,d]furan-1-yl)-N-phenyl-1,3-thiazole-4-carboxamide;

(2-(4-Methoxydibenzo[b,d]furan-1-yl)-1,3-thiazol-4-yl)(4-(pyrimidin-2-yl)piperazin-1-yl)methanone;

(2-(4-Methoxydibenzo[b,d]furan-1-yl)-1,3-thiazol-4-yl)(4-(pyridin-2-yl)piperazin-1-yl)methanone;

N-(4-Chlorophenyl)-2-(4-methoxydibenzo[b,d]furan-1-yl)-1,3-thiazole-4-carboxamide;

Ethyl 2-(4-methoxydibenzo[b,d]furan-1-yl)-4-methyl-1,3-thiazole-5-carboxylate;

2-(4-Methoxydibenzo[b,d]furan-1-yl)-4-(4-methoxyphenyl)-1,3-thiazole;

2-(4-Methoxydibenzo[b,d]furan-1-yl)-4-methyl-1,3-thiazole-5-carboxylic acid;

N-(3,5-Dichloropyridin-4-yl)-2-(4-methoxydibenzo[b,d]furan-1-yl)-4-methyl-1,3-thiazole-5-carboxamide;

2-(4-Methoxydibenzo[b,d]furan-1-yl)-1,3-thiazole-4-carboxamide;

N-Cyclopentyl-2-(4-methoxydibenzo[b,d]furan-1-yl)-5-methyl-1,3-thiazole-4-carboxamide;

N-(4-Hydroxycyclohexyl)-2-(4-methoxydibenzo[b,d]furan-1-yl)-5-methyl-1,3-thiazole-4-carboxamide;

N-(3,5-Dichloropyridin-4-yl)-2-(4-methoxydibenzo[b,d]furan-1-yl)-5-methyl-1,3-thiazole-4-carboxamide;

N-Ethyl-2-(4-methoxydibenzo[b,d]furan-1-yl]-5-methyl-1,3-thiazole-4-carboxamide;

2-(4-Methoxydibenzo[b,d]furan-1-yl)-N-morpholino-1,3-thiazole-4-carboxamide;

N-(4-Hydroxycyclohexyl)-2-(4-methoxydibenzo[b,d]furan-1-yl)-1,3-thiazole-4-carboxamide;

2-[4-(Difluoromethoxy)-8-nitrodibenzo[b,d]furan-1-yl]-5-methyl-1,3-thiazole-4-carboxylic acid;

2-(4-(Difluoromethoxy)-8-(methylsulfonamido)dibenzo[b,d]furan-1-yl)-5-methyl-1,3-thiazole-4-carboxylic acid;

N-(3,5-Dichloropyridin-4-yl)-2-(4-(difluoromethoxy)-8-(methylsulfonamido)dibenzo[b,d]furan-1-yl)-1,3-thiazole-4-carboxamide;

2-(4-(Difluoromethoxy)-8-(methylsulfonamido)dibenzo[b,d]furan-1-yl)-N-(4-hydroxycyclohexyl)-5-methyl-1,3-thiazole-4-carboxamide;

2-[8-(Acetylamino)-4-(difluoromethoxy)dibenzo[b,d]furan-1-yl]-1,3-thiazole-4-carboxylic acid;

2-(4-(Difluoromethoxy)-8-(methylsulfonamido)dibenzo[b,d]furan-1-yl)-N-methoxy-5-methyl-1,3-thiazole-4-carboxamide;

2-(8-Acetamido-4-(difluoromethoxy)dibenzo[b,d]furan-1-yl)-N-(4-hydroxycyclohexyl)-1,3-thiazole-4-carboxamide;

2-((4-Difluoromethoxy)dibenzo[b,d]furan-1-yl)-N-(4-hydroxycyclohexyl)-1,3-thiazole-4-carboxamide;

2-((4-Difluoromethoxy)dibenzo[b,d]furan-1-yl)-N-(2,2,2-trifluoroethyl)-1,3-thiazole-4-carboxamide;

2-(4-Methoxydibenzo[b,d]furan-1-yl)-N-(2,2,2-trifluoroethyl)-1,3-thiazole-4-carboxamide;

2-((4-Difluoromethoxy)dibenzo[b,d]furan-1-yl)-N-methoxy-1,3-thiazole-4-carboxamide;

2-[4-(Difluoromethoxy)-8-(trifluoromethyl)dibenzo[b,d]furan-1-yl]-1,3-thiazole-4-carboxylic acid;

2-(4-(Difluoromethoxy)-8-(trifluoromethyl)dibenzo[b,d]furan-1-yl)-N-(4-hydroxycyclohexyl)-1,3-thiazole-4-carboxamide;

(2-(4-(Difluoromethoxy)-8-(trifluoromethyl)dibenzo[b,d]furan-1-yl)-1,3-thiazol-4-yl)(4-hydroxypiperidin-1-yl)methanone;

2-(4-(Difluoromethoxy)-(methylsulfonamido)dibenzo[b,d]furan-1-yl)-N-(4-hydroxycyclohexyl)-1,3-thiazole-4-carboxamide;

Ethyl 2-(4-(difluoromethoxy)-8-nitrodibenzo[b,d]furan-1-yl)-1,3-oxazole-4-carboxylate;

Ethyl 2-(4-(difluoromethoxy)-8-(methylsulfonamido)dibenzo[b,d]furan-1-yl)-1,3-oxazole-4-carboxylate;

2-(4-(Difluoromethoxy)-8-(methylsulfonamido)dibenzo[b,d]furan-1-yl)-1,3-oxazole-4-carboxylic acid;

2-(4-(Difluoromethoxy)-8-(methylsulfonamido)dibenzo[b,d]furan-1-yl)-N-(4-hydroxycyclohexyl)-1,3-oxazole-4-carboxamide;

N-Cyclopropyl-2-(4-(difluoromethoxy)-8-[(methylsulfonyl)amino]dibenzo[b,d]furan-1-yl)-1,3-oxazole-4-carboxamide;

N-Cyclopentyl-2-(4-(difluoromethoxy)-8-(methylsulfonamido)dibenzo[b,d]furan-1-yl)-1,3-oxazole-4-carboxamide;

Ethyl 2-(4-methoxydibenzo[b,d]furan-1-yl)-5-methyl-1,3-oxazole-4-carboxylate;

2-(4-Methoxydibenzo[b,d]furan-1-yl)-5-methyl-1,3-oxazole-4-carboxylic acid;

N-(3,5-Dichloropyridin-4-yl)-2-(4-methoxydibenzo[b,d]furan-1-yl)-5-methyl-1,3-oxazole-4-carboxamide;

N-Cyclopropyl-2-(4-methoxydibenzo[b,d]furan-1-yl)-5-methyl-1,3-oxazole-4-carboxamide;

N-Ethyl-2-(4-methoxydibenzo[b,d]furan-1-yl)-5-methyl-1,3-oxazole-4-carboxamide;

2-(4-Methoxydibenzo[b,d]furan-1-yl)-5-methyl-1,3-oxazole-4-carboxamide;

N-Cyclopentyl-2-(4-methoxydibenzo[b,d]furan-1-yl)-5-methyl-1,3-oxazole-4-carboxamide;

N-(4-Hydroxycyclohexyl)-2-(4-methoxydibenzo[b,d]furan-1-yl)-5-methyl-1,3-oxazole-4-carboxamide;

2-(4-Methoxydibenzo[b,d]furan-1-yl)-5-methyl-N-(propan-2-yl)-1,3-oxazole-4-carboxamide;

Ethyl 2-(4-methoxydibenzo[b,d]furan-1-yl)-1,3-oxazole-4-carboxylate;

2-(4-Methoxydibenzo[b,d]furan-1-yl)-1,3-oxazole-4-carboxylic acid;

Ethyl 2-(4-(2-(4-methoxydibenzo[b,d]furan-1-yl)-1,3-oxazole-4-carbonyl)piperazin-1-yl)pyrimidine-5-carboxylate;

N-(3,5-Dichloropyridin-4-yl)-2-(4-methoxydibenzo[b,d]furan-1-yl)-1,3-oxazole-4-carboxamide;

2-(4-(2-(4-Methoxydibenzo[b,d]furan-1-yl)oxazole-4-carbonyl)piperazin-1-yl)pyrimidine-5-carboxylic acid;

2-(4-Methoxydibenzo[b,d]furan-1-yl)-1,3-oxazole-4-carboxamide;

[2-(4-Methoxydibenzo[b,d]furan-1-yl)-1,3-oxazol-4-yl](4-(pyrimidin-2-yl piperazin-1-yl)methanone;

2-(4-Methoxydibenzo[b,d]furan-1-yl)-N-methyl-1,3-oxazole-4-carboxamide;

N-Cyclopropyl-2-(4-methoxydibenzo[b,d]furan-1-yl)-1,3-oxazole-4-carboxamide;

[2-(4-Methoxydibenzo[b,d]furan-1-yl)-1,3-oxazol-4-yl](pyrrolidin-1-yl)methanone;

2-(4-Methoxydibenzo[b,d]furan-1-yl)-1,3-benzo[d]oxazole-5-carboxylic acid;

2-(4-Methoxydibenzo[b,d]furan-1-yl)-1,3-benzo[d]oxazole-5-carboxamide;

2-(4-Methoxydibenzo[b,d]furan-1-yl)-1,3-benzo[d]oxazole;

2-(4-Methoxydibenzo[b,d]furan-1-yl)[1,3]oxazolo[4,5-b]pyridine;

N-Cyclopentyl-2-(4-methoxydibenzo[b,d]furan-1-yl)-1,3-benzo[d]oxazole-5-carboxamide; and N-(4-Hydroxycyclohexyl)-2-(4-methoxydibenzo[b,d]furan-1-yl)-1,3-benzo[d]oxazole-5-carboxamide, or their pharmaceutically acceptable salts.

4. A pharmaceutical composition comprising a compound of formula (I) as claimed in claim 1, as an active ingredient along with a pharmaceutically acceptable carrier, diluent or excipient.

5. A pharmaceutical composition as claimed in claim 4, wherein the said composition is in the form of a tablet, capsule, powder, syrup, solution, aerosol or suspension.

6. A method of treating allergic or inflammatory diseases selected from asthma, COPD, chronic bronchitis, atopic dermatitis, allergic rhinitis, allergic conjunctivitis, vernal conjuctivitis, psoriasis, rheumatoid arthritis, ulcerative colitis, Crohn's disease, uveitis, NASH and lupus comprising administering an effective amount of a compound according to claim 1, to a mammal in need thereof.

7. A method of treatment of inflammatory diseases selected from asthma, COPD and chronic bronchitis comprising administering an effective amount of a compound according to claim 1, to a mammal in need thereof.

8. A pharmaceutical composition comprising a compound of formula (I) as claimed in claim 3, as an active ingredient along with a pharmaceutically acceptable carrier, diluent or excipient.

9. A method of treating allergic or inflammatory diseases selected from asthma, COPD, chronic bronchitis, atopic dermatitis, allergic rhinitis, allergic conjunctivitis, vernal conjuctivitis, psoriasis, rheumatoid arthritis, ulcerative colitis, Crohn's disease, uveitis, NASH and lupus comprising administering an effective amount of a compound according to claim 3, to a mammal in need thereof.

10. A method of treatment of inflammatory diseases selected from asthma, COPD and chronic bronchitis comprising administering an effective amount of a compound according to claim 3, to a mammal in need thereof.

* * * * *